United States Patent
Tal et al.

(10) Patent No.: US 9,999,767 B2
(45) Date of Patent: Jun. 19, 2018

(54) ESOPHAGEAL STIMULATION SYSTEM

(71) Applicants: Michael Gabriel Tal, Savyon (IL); Dvir Keren, Tel Aviv (IL); Amichay Haim Gross, Herzliya (IL)

(72) Inventors: Michael Gabriel Tal, Savyon (IL); Dvir Keren, Tel Aviv (IL); Amichay Haim Gross, Herzliya (IL)

(73) Assignee: E-MOTION MEDICAL, LTD., Tel-Aviv (IL)

( * ) Notice: Subject to any disclaimer, the term of this patent is extended or adjusted under 35 U.S.C. 154(b) by 0 days. days.

(21) Appl. No.: 14/847,675

(22) Filed: Sep. 8, 2015

(65) Prior Publication Data

US 2015/0374982 A1 Dec. 31, 2015

Related U.S. Application Data

(63) Continuation-in-part of application No. 13/533,805, filed on Jun. 26, 2012, now Pat. No. 9,149,629, and
(Continued)

(51) Int. Cl.
*A61N 1/36* (2006.01)
*A61N 1/05* (2006.01)

(52) U.S. Cl.
CPC ....... *A61N 1/36007* (2013.01); *A61N 1/0517* (2013.01)

(58) Field of Classification Search
CPC .......................... A61N 1/36007; A61N 1/0517
(Continued)

(56) References Cited

U.S. PATENT DOCUMENTS 3,411,507 A    11/1968   Wingrove
4,735,206 A    4/1988   Hewson
(Continued)

FOREIGN PATENT DOCUMENTS

JP    2011529766 A    12/2011
WO       9217150      10/1992
(Continued)

OTHER PUBLICATIONS

International Preliminary Report on Patentability dated Jan. 7, 2014 for PCT Application No. PCT/IB2012/001546.
(Continued)

*Primary Examiner* — Carl H Layno
*Assistant Examiner* — Erin M Piateski
(74) *Attorney, Agent, or Firm* — Clements Bernard Walker PLLC; Christopher L. Bernard

(57) ABSTRACT

System for generating a distally traveling synthetic esophageal motion within a subject's esophagus. Includes: elongated member sized and configured for nasal or oral placement into the esophagus; series of stimulators mounted/mountable on and distributed along a length of elongated member, for stimulating portions along an esophageal length spanning between esophagus LES and UES, and include at least two longitudinally spaced electrodes, chargeable to opposite polarities; and signal generator for generating and sending sequences of stimulating signals to stimulators, to evoke a plurality of local esophageal contractions as distally traveling synthetic esophageal motion along the esophageal length. Also disclosed is an implant suitable for use in generating a distally traveling synthetic esophageal motion within a subject's esophagus, for example, suitable for use in the disclosed system. Exemplary applications include for treating an esophagus exhibiting different physiological con-
(Continued)

ditions or/and characteristics, for example, of suspended esophageal peristaltic motility.

27 Claims, 12 Drawing Sheets

Related U.S. Application Data a continuation-in-part of application No. 14/655,067, filed as application No. PCT/US2013/077261 on Dec. 20, 2013.

(60) Provisional application No. 61/501,338, filed on Jun. 27, 2011, provisional application No. 61/612,072, filed on Mar. 16, 2012, provisional application No. 61/745,751, filed on Dec. 24, 2012.

(58) Field of Classification Search
USPC .......................................................... 607/40
See application file for complete search history.

(56) References Cited

U.S. PATENT DOCUMENTS

| | | | |
|---|---|---|---|
| 5,540,730 A | 7/1996 | Terry, Jr. et al. | |
| 5,690,691 A | 11/1997 | Chen | |
| 5,716,385 A | 2/1998 | Mittal et al. | |
| 5,725,564 A | 3/1998 | Freed et al. | |
| 5,814,092 A * | 9/1998 | King ................. | A61N 1/36071 607/46 |
| 5,836,994 A | 11/1998 | Bourgeois | |
| 5,891,185 A | 4/1999 | Freed et al. | |
| 6,010,453 A | 1/2000 | Fiddian-Green | |
| 6,097,984 A | 8/2000 | Douglas | |
| 6,148,222 A | 11/2000 | Ramsey | |
| 6,591,137 B1 * | 7/2003 | Fischell ............ | A61N 1/36007 607/133 |
| 6,754,536 B2 | 6/2004 | Swoyer et al. | |
| 6,773,452 B2 | 8/2004 | Shaker | |
| 6,895,279 B2 | 5/2005 | Loeb et al. | |
| 7,167,750 B2 | 1/2007 | Knudson et al. | |
| 7,343,201 B2 | 3/2008 | Mintchev | |
| 7,402,172 B2 | 7/2008 | Chin et al. | |
| 7,416,546 B2 | 8/2008 | Pugsley et al. | |
| 7,606,623 B2 | 10/2009 | Ludlow et al. | |
| 7,660,636 B2 | 2/2010 | Castel et al. | |
| 7,720,539 B2 | 5/2010 | Mintchev | |
| 7,738,961 B2 | 6/2010 | Sharma | |
| 7,794,425 B2 | 9/2010 | Gobel | |
| 8,032,222 B2 | 10/2011 | Loushin et al. | |
| 8,092,433 B2 | 1/2012 | Hamdy | |
| 8,209,034 B2 | 6/2012 | Simon et al. | |
| 8,275,460 B2 | 9/2012 | Loushin et al. | |
| 8,447,403 B2 | 5/2013 | Sharma et al. | |
| 8,447,404 B2 | 5/2013 | Sharma et al. | |
| 8,603,188 B2 | 12/2013 | Behan | |
| 8,876,762 B2 | 11/2014 | Dayan et al. | |
| 2001/0053920 A1 * | 12/2001 | Shaker ................ | A61B 5/037 606/197 |
| 2006/0247717 A1 | 11/2006 | Starkebaum | |
| 2006/0265021 A1 | 11/2006 | Herbert | |
| 2007/0073361 A1 | 3/2007 | Goren et al. | |
| 2007/0185540 A1 | 8/2007 | Ben-Haim et al. | |
| 2007/0225576 A1 | 9/2007 | Brown et al. | |
| 2007/0225617 A1 | 9/2007 | Mabary et al. | |
| 2007/0293926 A1 | 12/2007 | Dunlay et al. | |
| 2008/0009810 A1 | 1/2008 | Hamdy | |
| 2008/0167675 A1 * | 7/2008 | Hogosta ............. | A61B 5/037 606/196 |
| 2008/0249507 A1 | 10/2008 | Hadani | |
| 2008/0312712 A1 | 12/2008 | Penner | |
| 2008/0319504 A1 * | 12/2008 | Loushin ............. | A61N 1/0517 607/40 |
| 2009/0018602 A1 | 1/2009 | Mitelberg et al. | |
| 2009/0030475 A1 | 1/2009 | Brynelsen et al. | |
| 2009/0062725 A1 | 3/2009 | Goebel | |
| 2009/0132001 A1 * | 5/2009 | Soffer ................ | A61N 1/36007 607/40 |
| 2009/0143651 A1 | 6/2009 | Kallback et al. | |
| 2009/0259274 A1 | 10/2009 | Simon et al. | |
| 2010/0030133 A1 | 2/2010 | Elia et al. | |
| 2010/0087715 A1 | 4/2010 | Van Bommel et al. | |
| 2010/0160996 A1 | 6/2010 | Simon et al. | |
| 2010/0217368 A1 | 8/2010 | Dinsmoor et al. | |
| 2010/0241191 A1 | 9/2010 | Testerman et al. | |
| 2010/0305655 A1 | 12/2010 | Raffle et al. | |
| 2011/0004266 A1 | 1/2011 | Sharma | |
| 2011/0034967 A1 | 2/2011 | Chen et al. | |
| 2011/0130650 A1 | 6/2011 | Dayan et al. | |
| 2011/0144481 A1 | 6/2011 | Feer et al. | |
| 2013/0012920 A1 | 1/2013 | Elia et al. | |
| 2013/0014761 A1 | 1/2013 | Elia et al. | |
| 2013/0131753 A1 | 5/2013 | Simon et al. | |
| 2013/0158514 A1 | 6/2013 | Elia et al. | |
| 2013/0197321 A1 | 8/2013 | Wilson | |
| 2013/0231753 A1 | 9/2013 | Liddy et al. | |
| 2014/0236262 A1 | 8/2014 | You et al. | |
| 2014/0330076 A1 | 11/2014 | Elia et al. | |

FOREIGN PATENT DOCUMENTS

| | | |
|---|---|---|
| WO | 2005007120 A2 | 1/2005 |
| WO | 2005051486 A1 | 6/2005 |
| WO | 2006060458 | 6/2006 |
| WO | 2008088985 A2 | 7/2008 |
| WO | 2008104982 A2 | 9/2008 |
| WO | 2010016054 A1 | 2/2010 |
| WO | 2012131303 | 10/2012 |
| WO | 2014009950 A1 | 1/2014 |
| WO | 2014041532 A1 | 3/2014 |
| WO | 2014105759 | 7/2014 |
| WO | 2014105759 A1 | 7/2014 |

OTHER PUBLICATIONS

International Search Report and Written Opinion dated Jun. 20, 2014 for PCT Application No. PCT/US2013/077261.

Paterson: "Esophageal peristalsis", GI Motility online. Retrieved from internet URL: http://www. nature.com/gimo/contents/ptl/full/gimo13/html on Mar. 5, 2014.

International Search Report and Written Opinion dated Oct. 30, 2012 received in PCT Application PCT/IB2012/001546.

Lee et al., "Changes in gastroesophageal reflux in patients with nasogastric tube followed by percutaneous endoscopic gastrostomy," J. Formos Med Assoc 20 II; II 0(2): 115-19.

Manning et al., "Nasogastric intubation causes gastroesophageal reflux in patients undergoing elective laparotomy," Surgery 2001; 130(5): 788-91.

Torres et al., "Stomach as a source of colonization of the respiratory tract during mechanical ventilation: association with ventilator-associated pneumonia," European Respiratory Journal 1996; 9(8): 1729-35.

Ibanez et al., "Gastroesophageal reflux in intubated patients receiving enteral nutrition: effect of supine and semirecumbent positions," Journal of Parenteral and Enteral Nutrition 1992; 16(5): 419-22.

Pellegrini et al., "Gastroesophageal reflux and pulmonary aspiration: incidence, functional abnormality, and results of surgical therapy," Surgery 1979; 86(1 ): II0-19.

Guelrud et al., "Transcutaneous Electrical Nerve Stimulation Decreases Lower Esophageal Sphincter Pressure in Patients with Achalasia," Digestive Diseases amd Sciences, vol. 36, No. 8, Aug. 1991, pp. 1029-1033.

Medscape, Postoperative Ileus,article, Jan. 5, 2016,https://search.medscape.com/search/?q=Burt%20Cagir.

Medscape, Postoperative Ileus Treatment & Management,article, Jan. 5, 2016https://search.medscape.com/search/?q =Burt%20Cagir.

* cited by examiner

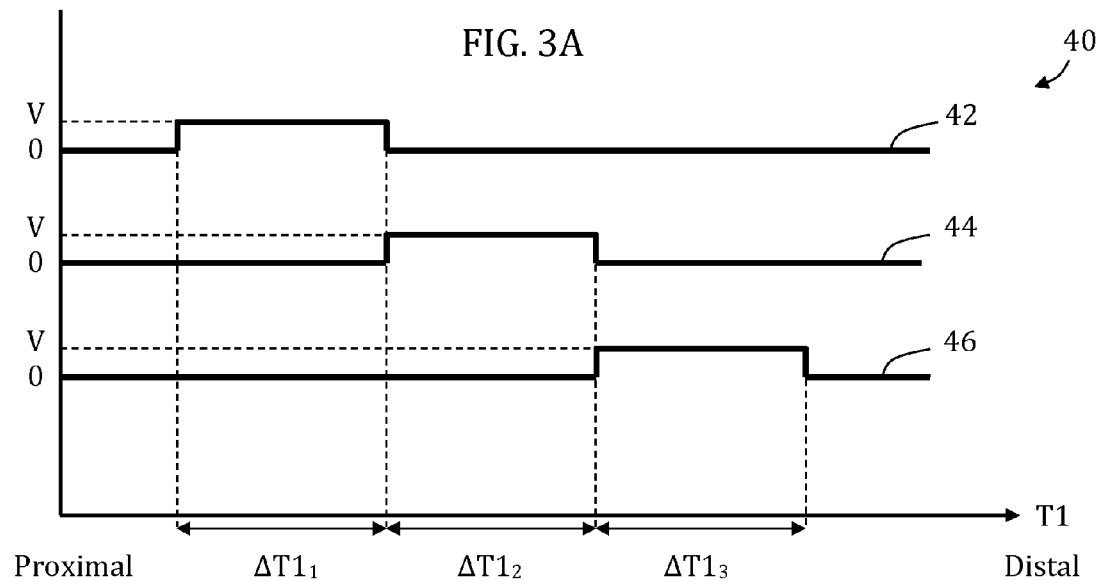
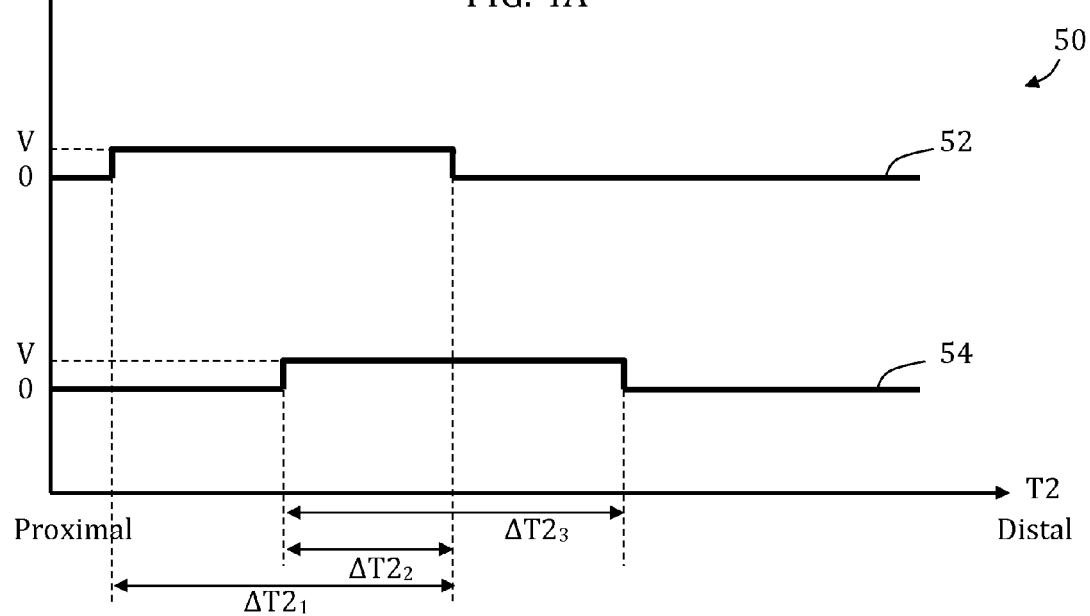

ESOPHAGEAL STIMULATION SYSTEM

RELATED APPLICATIONS

This application is a continuation-in-part (CIP) of U.S. Pat. No. 9,149,629, issued Oct. 6, 2015, entitled "ESOPHAGEAL STIMULATION DEVICES AND METHODS", which claims the benefit of priority from U.S. Provisional Patent Application No. 61/501,338, filed on Jun. 27, 2011, and U.S. Provisional Patent Application No. 61/612,072, filed on Mar. 16, 2012, both entitled "ESOPHAGEAL STIMULATION DEVICE"; and a continuation-in-part (CIP) of U.S. patent application Ser. No. 14/655,067, filed on Jun. 24, 2015 entitled "GI TRACT STIMULATION DEVICES AND METHODS", which is a National Phase of PCT Patent Application No. PCT/US2013/077261 having an International filing date of Dec. 20, 2013, which claims the benefit of priority under 35 USC § 119(e) of U.S. Provisional Patent Application No. 61/745,751, filed on Dec. 24, 2012. The contents of all the above applications are fully incorporated herein by reference as if fully set forth herein.

FIELD OF THE INVENTION

The present invention, in some embodiments thereof, relates to techniques for generating motility in gastrointestinal (GI) organs in a subject, and in particular, to techniques for generating esophageal motility that result in diminishing retrograde flow of gastric contents in a subject's GI tract. Some embodiments of the present invention relate to a system for generating a distally traveling synthetic esophageal motion within a subject's esophagus. Some embodiments of the present invention relate to an implant suitable for use in generating a distally traveling synthetic esophageal motion within a subject's esophagus. In exemplary embodiments, the disclosed implant is suitable for use in the disclosed system.

BACKGROUND OF THE INVENTION

The esophagus is a tubular muscular organ having a length of approximately 25 cm, located between the upper esophageal sphincter (UES) and the lower esophageal sphincter (LES). The esophagus functions solely to deliver food from the mouth to the stomach using peristaltic muscle motion. Peristalsis is a sequential, coordinated contraction wave that travels the entire length of the esophagus, propelling intraluminal contents distally to the stomach. Primary peristalsis is the peristaltic wave triggered by the swallowing center. The peristaltic contraction wave travels at a speed of approximately 2 cm/s and correlates with manometry-recorded contractions. The secondary peristaltic wave is induced by esophageal distension from the retained bolus, refluxed material, or swallowed air, with the primary role to clear the esophagus of retained food or any gastroesophageal refluxate. Tertiary contractions are simultaneous, isolated, dysfunctional contractions. Anesthetization or sedation are suspected of causing suspension of esophageal peristaltic motility and lowers LES pressure, hence gastric content are more prone to infiltrate and travel proximally in the esophagus.

Gastric contents refluxing through the esophagus are known to affect conditions which may increase morbidity and mortality rates. Gastroesophageal Reflux (GER) is a condition, in which the LES opens spontaneously, for varying periods of time, or does not close properly and stomach contents rise up into the esophagus. In Laryngopharyngeal Reflux (LPR), the retrograde flow of gastric contents reaches the upper aero-digestive tract. In order to diminish and treat such conditions, efforts have been made to develop medical and surgical means for improving LES functionality and for creating a substitute sphincter proximally adjacent the stomach. In some occasions it may be advantageous to develop a second "line of defense" provided proximally to the LES along the esophagus, especially to push back any gastric contents or chyme that infiltrated the LES or any substitute or supplement thereof. Such a need may arise, for example, in cases of intubation and/or ventilation, usually in anesthetized ICU patients, CVA patients, or others, in which esophageal motility is muted or less dominant.

Tube feeding (e.g., gastric feeding, or enteral feeding) is a common and life preserving procedure, however, complications can arise. GER is commonly associated with tube feeding, including in usage of nasogastric tubing (NGT) and other gastric feeding practices. Research in past years has discussed the emergence of GER as an effect of the use of NGT, for example, as disclosed in Ibanez et al., "Gastroesophageal reflux in intubated patients receiving enteral nutrition: effect of supine and semirecumbent positions", *JPEN J Parenter Enteral Nutr.* 1992 September-October; 16(5): 419-22; in Manning et al., "Nasogastric intubation causes gastroesophageal reflux in patients undergoing elective laparotomy", *Surgery.* 2001 November; 130(5):788-91 and in Lee et al., "Changes in gastroesophageal reflux in patients with nasogastric tube followed by percutaneous endoscopic gastrostomy", *J Formos Med Assoc.* 2011 February; 110(2): 115-9.

Pulmonary aspiration is the entry of material from the oropharynx or gastrointestinal tract into the larynx and lower respiratory tract. Consequences of pulmonary aspiration range from no injury at all, to chemical pneumonitis or pneumonia, to death within minutes from asphyxiation. One common cause of pulmonary aspiration is aspiration of gastric contents, as suggested in relevant literature, for example. Pellegrini el al., "Gastroesophageal reflux and pulmonary aspiration: incidence, functional abnormality, and results of surgical therapy". *Surgery.* 1979 July; 86(1): 110-9, indicating that incidence of aspiration is due to a motor disorder that interferes with the ability of the esophagus to clear refluxed acid, and that abnormal pulmonary symptoms can induce or result from gastroesophageal reflux.

Ventilator-associated pneumonia (VAP) is pneumonia that develops 48 hours or longer after mechanical ventilation is given by means of an endotracheal tube or tracheostomy. VAP results from the invasion of microorganisms into the lower respiratory tract and lung parenchyma. Intubation compromises the integrity of the oropharynx and trachea and allows oral and gastric secretions to enter the lower airways. The aetiopathogenesis of VAP requires abnormal oropharyngeal and gastric colonization and the further aspiration of their contents to the lower airways. Known risk factors for gastric colonization include: alterations in gastric juice secretion; alkalinization of gastric contents; administration of enteral nutrition; administration of antacids; and the presence of bilirubin. According to Torres et al. (in "Stomach as a source of colonization of the respiratory tract during mechanical ventilation: association with ventilator-associated pneumonia", *Eur Respir J.* 1996 August; 9(8):1729-35), although the role of the colonized gastric reservoir in the development of VAP remains debatable, there is major evidence in the literature in favor of the gastric origin of part of these pulmonary infections.

US Patent Appln. Publication No. 2011/0130650 A1 relates to an enteral feeding device comprising "expandable means which prevents or significantly reduces aspirations from the alimentary tract to the respiratory system. In further aspects, the invention relates to systems comprising said enteral feeding device, methods and uses thereof.".

US Patent Appln. Publication No. 2010/0160996 A1 relates to methods and apparatuses for treating ailments by "inserting a balloon-electrode device into an esophagus of a mammal, the balloon-electrode device including: (i) a nasogastral (NG) tube having an internal passageway and an external surface, (ii) at least one electrode coupled to the external surface of the NG tube, (iii) a conductor extending through the internal passageway of the NG tube and electrically connecting to the electrode, and (iv) a balloon surrounding the electrode and a portion of the NG tube; inflating the balloon with fluid such that the electrode is substantially centrally located within an interior volume of the balloon; and applying at least one electrical signal to the electrode via the conductor such that an electromagnetic field emanates from the electrode to at least one of nerves and muscles of the mammal".

US Patent Appln. Publication No. 2008/0249507 A1 relates to a "food administering apparatus including a feeding tube, having a distal outlet and proximal inlet, adapted for insertion of the distal outlet into the stomach of an adult patient while the proximal inlet is outside the patient, the tube being suitable for administering food or medicine from a proximal port to the distal outlet and at least one electrode mounted on the tube".

US Patent Appln. Publication No. 2008/0319504 A1 relates to a "device for stimulating select body tissues and organs from within a compartment in a body. The device includes a tube and at least one distendable element configured to expand against the compartment into a first position and contract within the compartment into a second position. At least one electrical component is in association with each of the distendable elements and configured to activate and deactivate electrical stimulation to the select body tissues and organs. The expansion and contraction of each distendable element and the activation and deactivation of each electrical component in the compartment is repeated over a period of time.".

The same applicant/assignee of the present disclosure developed techniques for generating motility in a subject's gastrointestinal (GI) tract and organs thereof, including, for example, techniques for generating esophageal motility in a subject. Exemplary teachings and practices of such techniques are provided in same applicant/assignee disclosures: U.S. Patent Appln. Publication No. US 2013/0006323 A1, and PCT Int'l. Patent Appln. Publication No. WO 2014/105759 A1.

In spite of such teachings in the field of the invention, there is an on-going need for developing and practicing improved or/and new techniques for generating esophageal motility in a subject's gastrointestinal (GI) tract.

SUMMARY OF THE INVENTION

The present invention, in some embodiments thereof, relates to techniques for generating esophageal motility that result in diminishing retrograde flow of gastric contents in a subject's gastrointestinal (GI) tract. Some embodiments of the present invention relate to a system for generating a distally traveling synthetic esophageal motion within a subject's esophagus. Some embodiments of the present invention relate to an implant suitable for use in generating a distally traveling synthetic esophageal motion within a subject's esophagus. In exemplary embodiments, the disclosed implant is suitable for use in the disclosed system. In exemplary embodiments, the disclosed system, and components thereof, are particularly applicable for generating the distally traveling synthetic esophageal motion within the subject's esophagus, wherein the esophagus exhibits different physiological conditions or/and characteristics, for example, wherein the esophagus exhibits characteristics of suspended esophageal peristaltic motility.

According to an aspect of some embodiments of the present invention, there is provided a system for generating a distally traveling synthetic esophageal motion within a subject's esophagus, the system comprising: an elongated member sized and configured for nasal or oral placement into the esophagus; a series of stimulators mounted or mountable on the elongated member and distributed along a length of the elongated member, the series of stimulators is configured for stimulating a series of portions of the esophagus along an esophageal length spanning between the esophagus LES and UES, and includes at least two longitudinally spaced electrodes, chargeable to opposite polarities; and a signal generator configured for generating and sending a sequence of stimulating signals to the series of stimulators, so as to evoke a plurality of local esophageal contractions in a form of a distally traveling synthetic esophageal motion along the esophageal length.

According to some embodiments of the invention, the signal generator is configured for developing local esophageal pressures of at least 40 mmHg for each of the local esophageal contractions.

According to some embodiments of the invention, the elongated member is a medical intubation device, for example, a gastric feeding tube.

According to some embodiments of the invention, the series of stimulators is fixed to the elongated member.

According to some embodiments of the invention, the elongated member includes at least one sensor mounted or mountable on the elongated member.

According to some embodiments of the invention, the at least one the sensor is mounted on the elongated member distally to a distal-most stimulator. According to some embodiments of the invention, the at least one sensor comprises at least one of: a pH sensor, a pressure sensor, a manometer, an impedance sensor, a motion sensor, a capacitance sensor, and a mechanical sensor.

According to some embodiments of the invention, the sequence of stimulating signals includes at least one electrical pulse or electrical pulse train having a magnitude higher than a stimulating threshold in a range of between about 5V and about 20V.

According to some embodiments of the invention, the signal generator is operatively connected to a control unit.

According to some embodiments of the invention, the control unit is configured and operative for controlling the signal generator to produce the sequence of stimulating signals being staggered in time such that distally-located stimulators receive stimulating signals after more proximally-located stimulators. According to some embodiments of the invention, the control unit is configured and operative for controlling the signal generator to selectively transition the series of stimulators among three states of electrical connectivity. According to some embodiments of the invention, the three states correspond to: (i) the series of stimulators connected to the signal generator, (ii) the series of stimulators connected to ground, and (iii) the series of stimulators not connected to the signal generator.

According to some embodiments of the invention, the plurality of local esophageal contractions is in a form of a wave of distally progressing contractions within the esophagus. According to some embodiments of the invention, the wave of distally progressing contractions includes a second wave starting only after a first wave is finished, without overlapping of the second and first waves. According to some embodiments of the invention, the wave of distally progressing contractions includes a second wave beginning before a first wave completes travelling from upper portion of the esophagus.

According to some embodiments of the invention, the control unit is configured and operative for controlling the signal generator to generate the sequence of stimulating signals in a form of a plurality of electrical pulses, each of the electrical pulses has a pulse current in a range of between about 10 milliamperes and about 50 milliamperes, and a pulse duration in a range of between about 0.01 millisecond and about 0.5 millisecond.

According to some embodiments of the invention, each of the electrical pulses has a pulse frequency in a range of between about 25 Hz and about 150 Hz. According to some embodiments of the invention, each of the electrical pulses is separated from an adjacent one of the electrical pulses by a time span of at least about 0.5 second. According to some embodiments of the invention, the plurality of electrical pulses is produced as part of a plurality of electrical pulse trains, whereby each of the electrical pulse trains comprises a number of the electrical pulses, and whereby each of the electrical pulse trains has a train pulse duration in a range of between about 0.5 second and about 5 seconds. According to some embodiments of the invention, each of the electrical pulse trains is separated from an adjacent one of the electrical pulse trains by a separation time span having a range of between about 0.5 minute and about 60 minutes.

According to some embodiments of the invention, the series of stimulators includes an even number of bipolar electrode pairs in a range of between four bipolar electrode pairs and twenty bipolar electrode pairs. According to some embodiments of the invention, the bipolar electrodes pairs are distributable such that a proximal-most electrode pair is locatable proximally to the UES. According to some embodiments of the invention, the bipolar electrodes pairs are distributable such that a distal-most electrode pair is locatable distally to the LES.

According to some embodiments of the invention, the system is configured for generating the distally traveling synthetic esophageal motion wherein the esophagus exhibits characteristics of suspended esophageal peristaltic motility.

According to an aspect of some embodiments of the present invention, there is provided an implant suitable for use in generating a distally traveling synthetic esophageal motion within a subject's esophagus, the implant comprising: an elongated member sized and configured for nasal or oral placement into the esophagus; and a series of stimulators fixed to the elongated member and distributed along a length of the elongated member, the series of stimulators is configured for stimulating a series of portions of the esophagus along an esophageal length spanning between the esophagus LES and UES, and includes at least two longitudinally spaced electrodes, chargeable to opposite polarities; wherein the elongated member is connectable to a signal generator configured for generating and sending a sequence of stimulating signals to the series of stimulators, so as to evoke a plurality of local esophageal contractions in a form of a distally traveling synthetic esophageal motion along the esophageal length.

According to some embodiments of the invention, for the implant, the elongated member is a medical intubation device.

According to some embodiments of the invention, for the implant, the series of stimulators includes an even number of bipolar electrode pairs in a range of between four bipolar electrode pairs and twenty bipolar electrode pairs. According to some embodiments of the invention, the series of stimulators is configured and operative to receive the sequence of stimulating signals from the signal generator.

According to some embodiments of the invention, for the implant, the series of stimulators is configured and operative to receive the sequence of stimulating signals being staggered in time such that distally-located stimulators receive stimulating signals after more proximally-located stimulators. According to some embodiments of the invention, for the implant, the series of stimulators is configured and operative to receive the sequence of stimulating signals from the signal generator that is operatively connected to a control unit.

According to some embodiments of the invention, the implant, the implant is configured and operative for use in generating the distally traveling synthetic esophageal motion wherein the esophagus exhibits characteristics of suspended esophageal peristaltic motility.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using an operating system.

For example, hardware for performing selected tasks according to embodiments of the invention could be implemented as a chip, as a circuit, or a combination thereof. As software, selected tasks of some embodiments of the invention could be implemented as a plurality of software instructions being executed by a computer using any suitable operating system. In an exemplary embodiment of the invention, one or more tasks of exemplary embodiments of the method or/and system as described herein are performed by a data processor, such as a computing platform for executing a plurality of instructions. Optionally, the data processor includes a volatile memory for storing instructions or/and data. Alternatively or additionally, optionally, the data processor includes a non-volatile storage, for example, a magnetic hard-disk or/and removable media, for storing instructions or/and data. Optionally, a network connection is provided as well. Optionally, a display or/and a user input device such as a keyboard or mouse is provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of various embodiments. In this regard, the description taken with the drawings makes apparent to those skilled in the art how embodiments of the invention may be practiced. In the drawings:

FIGS. 3A-3D schematically illustrate a first exemplary stimulation sequence and a correspondingly (synthetically) generated patterned esophageal motion, in accordance with some embodiments of the invention;

FIGS. 4A-4D schematically illustrate a second exemplary stimulation sequence and a correspondingly (synthetically) generated patterned esophageal motion, in accordance with some embodiments of the invention;

DESCRIPTION OF SPECIFIC EMBODIMENTS OF THE INVENTION

Figure 1A:
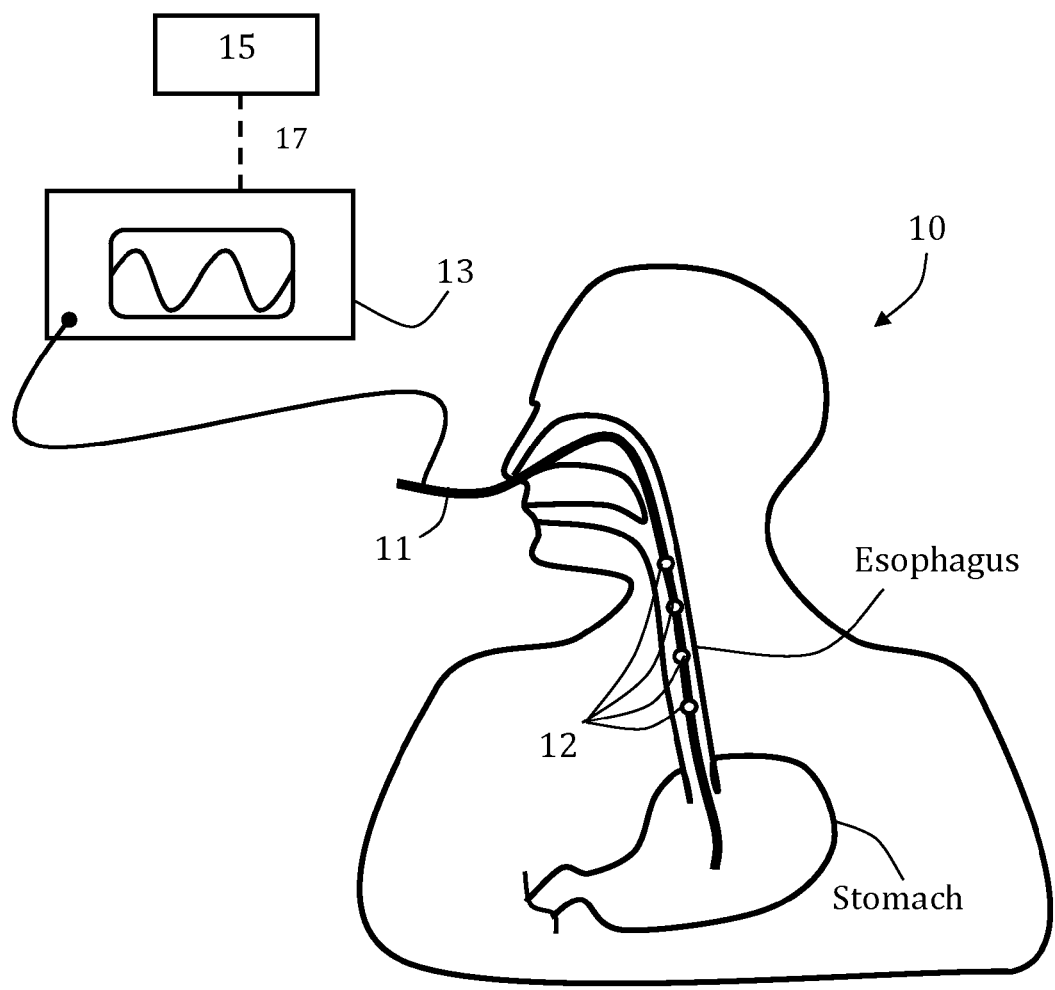
FIG. 1A schematically illustrates an exemplary nasogastric tube positioned in a patient's esophagus and including a plurality (series) of stimulators, in accordance with some embodiments of the invention.

The present invention, in some embodiments thereof, relates to techniques for generating esophageal motility that result in diminishing retrograde flow of gastric contents in a subject's gastrointestinal (GI) tract. Some embodiments of the present invention relate to a system for generating a distally traveling synthetic esophageal motion within a subject's esophagus. Some embodiments of the present invention relate to an implant suitable for use in generating a distally traveling synthetic esophageal motion within a subject's esophagus. In exemplary embodiments, the disclosed implant is suitable for use in the disclosed system. In exemplary embodiments, the disclosed implant is suitable for use in the disclosed system. In exemplary embodiments, the disclosed system, and components thereof, are particularly applicable for generating the distally traveling synthetic esophageal motion within the subject's esophagus, wherein the esophagus exhibits different physiological conditions or/and characteristics, for example, wherein the esophagus exhibits characteristics of suspended esophageal peristaltic motility.

Some embodiments of the present invention relate to a system, and components thereof, for initiating or/and sustaining minimal function of at least a portion of the GI tract. Such embodiments involve synthetically generating movement in one or more GI organs, including, for example, at least esophageal motility for diminishing retrograde flow of gastric contents or/and for promoting gastric digestion. Exemplary embodiments illustratively described herein may be used for synthetically stimulating any GI organ, such as, but not limited to, the: esophagus, gullet, stomach wall, pylorus, duodenum, jejunum, ileum, small intestine, caecum, colon, rectum, and large intestine.

In exemplary embodiments, the system is configured and operative for synthetically generating a patterned esophageal motion. A synthetically generated patterned esophageal motion may be any local or cross-esophageal muscular expansion or contraction, or any combination thereof, synthetically evoked or/and orchestrated following generated stimulation. The synthetic pattern may be a chosen form, shape, or/and magnitude of a plurality of local esophagus contractions in a form of a distally traveling and progressive synthetic esophageal motion along a length of the esophagus. In exemplary embodiments, such local esophageal contractions are in a form of a wave of distally progressing contractions within the esophagus, and have chosen characteristics, including but not limited to contraction force, wave travel velocity, and wave occurrence frequency. In some embodiments, the synthetically generated patterned esophageal motion corresponds to a synthetic type of peristalsis, for example, that simulates (mimics) a naturally occurring esophageal peristalsis. In exemplary embodiments, the synthetically generated patterned esophageal motion creates a synthetic type of peristalsis based on an algorithmic sequence of stimulations effected in a patient's esophagus.

According to an aspect of some embodiments of the invention, there is provided a system for generating a distally traveling synthetic esophageal motion within a subject's esophagus. In exemplary embodiments, the system includes: an elongated member sized and configured for nasal or oral placement into the esophagus; a series of stimulators mounted or mountable on the elongated member and distributed along a length of the elongated member, wherein the series of stimulators is configured for stimulating a series of portions of the esophagus along an esophageal length spanning between the esophagus LES and UES, and includes at least two longitudinally spaced electrodes, chargeable to opposite polarities; and a signal generator configured for generating and sending a sequence of stimulating signals to the series of stimulators, so as to evoke a plurality of local esophageal contractions in a form of a distally traveling synthetic esophageal motion along the esophageal length.

In exemplary embodiments, the elongated member and the series of stimulators are system components that may be configured and operative together as a 'self-contained', 'stand-alone', and 'connectable', device or apparatus, for example, as an implant, corresponding to a (structural/functional) sub-combination of exemplary embodiments of the herein disclosed system. In exemplary embodiments, such an implant is suitable for use, for example, as part of the herein disclosed system, in generating a distally traveling synthetic esophageal motion within a subject's esophagus. For example, such an implant is operatively [electrically/electronically] connectable (linkable) to a signal generator (for example, that is operatively connected to a control unit), thereby forming exemplary embodiments of a system for generating a distally traveling synthetic esophageal motion within a subject's esophagus. Thus, according to an aspect of some embodiments of the invention, there is provided an implant suitable for use in generating a distally traveling synthetic esophageal motion within a subject's esophagus.

In exemplary embodiments, the longitudinally spaced electrodes are configured for electrically stimulating adjacent/contacting esophagus muscle tissue. A stimulating electrode may be operatively connectable or provided readily connected with a generator, for example, an electrical pulse generator, configured to generate a chosen sequence of electrical stimulations. Optionally, alternatively or additionally, an internal power or/and signal source may be provided with the system that is sized and configured for intra-body (e.g., intra-orally) placement, for example, in or adjacent to the esophagus. In exemplary embodiments, a power or/and signal source may be provided (e.g., worn) on the patient. In exemplary embodiments, at least one electrode or/and sensor is operatively connected with such an internal power source sized and configured for placement on a medical intubation device (e.g., a feeding tube or other elongated tube, which extends through a patient's nose or mouth into at least the esophagus, and optionally, through the esophagus into the stomach or small intestine). In some embodiments, the system includes a plurality of stimulators provided at different relative locations within the esophagus.

A local contraction of the esophagus, or any combination or pattern of esophageal contractions may increase local or/and average esophageal pressure. Optionally, alternatively or additionally, electrical stimulation is used to decrease local or/and average volume entrapped along the esophagus lumen between the LES and the UES, optionally, also elsewhere along the GI tract, thereby increasing local or/and average pressure. By increasing the pressure at a local segment of the esophagus lumen, for example, a retrograded material or chyme if present may be forced to travel backward to a distal lumen segment being less pressured, whereas by increasing the average or overall pressure in the esophagus, a possible reflux causing positive pressure difference between the stomach and the esophagus may be diminished and even reversed, thereby diminishing the possibility or volume of refluxed material or even preventing reflux. In some embodiments, a local or/and average pressure caused by a single synthetically evoked contraction or a series of synthetically evoked contractions may be equal to or higher than 15 mmHg, optionally, equal to or higher than 25 mmHg, optionally, equal to or higher than 50 mmHg, and optionally, equal to or higher than 100 mmHg, or lower, higher, or intermediate to any of these values.

In some embodiments, the plurality or series of stimulators is fixed to the medical intubation device. Optionally, alternatively or additionally, the plurality or series of stimulators is provided with a fixator configured for fixedly covering a portion of the medical intubation device. The fixator may be slidably movable along a length of the medical intubation device or/and may be restrainedly securable around the portion of the medical intubation device. In some embodiments, the fixator is fixedly lockable to the portion of the medical intubation device thereby preventing sliding therealong.

In some embodiments, the series of stimulators is, or includes, at least two stimulators that are sequentially positioned along an esophageal length, each stimulator being configured stimulate a different esophageal portion. In exemplary embodiments, the plurality or series of stimulators is provided along the effective length of the medical intubation device. In exemplary embodiments, an effective length (esophageal length) is configured for positioning in a defined segment of the esophagus; while alternatively, an effective length (esophageal length) may be configured to include at least a segment along the esophagus and at least another segment in a distinct GI organ, for example, the intestines, either continuously to the esophagus segment or discontinuously thereto.

In exemplary embodiments, wherein the series of stimulators is, or includes, a plurality of at least two longitudinally spaced electrodes, the electrodes are arranged in groups referred to herein as terminals. In some embodiments, two electrodes (i.e., electrodes pairs) or more form a terminal. In some such embodiments, one electrode is a positive electrode, which receives current from a signal generator, and the other electrode is a negative electrode, which is grounded. The distance between each terminal may be fixed or variable, and the terminals are spaced such that the distance between each terminal is greater than the distance between each electrode within any given terminal. For example, the width of the terminal (i.e., the distance between the electrodes of a terminal) may be 5-10 mm, and optionally, 8 mm. The distance between each terminal may be 15-30 mm, optionally, 20 mm, or optionally, below, above, or intermediate to these values. Optionally, additionally, or alternatively, at least some electrodes are arranged in same distance therebetween so that a width of a terminal equals the distance between each terminal. In some such embodiments, the distance between each adjacent electrodes/terminals is at least 5 mm, optionally, at least 10 mm, optionally, at least 20 mm, optionally, at least 30 mm, or higher, or lower, or intermediate value. In other embodiments having two electrodes per terminal, the system also includes an array of controlled relays coupled to the electrodes. The array of controlled relays may be configured to selectively transition each electrode between a positively connected state, a grounded state, and a disconnected state. In still other embodiments, three electrodes form a terminal. In such embodiments, two of the electrodes may be grounded, and the third electrode, which is positioned between the two grounded electrodes, may be a positive electrode connected to a signal generator. The electrodes are positioned such that the positive electrode will close a circuit with the two negative (grounded) electrodes of the same terminal. Such a design may position the center of stimulation at the location of the positive electrode.

In some embodiments, the system further includes at least one sensor. Optionally, the sensor is provided on the medical intubation device distally to the series of stimulators. Optionally, the sensor is a pH sensor, for example, adapted to sense a change (e.g., decrease) of local pH, for example, due to the presence of gastric contents proximally to the LES. Optionally, alternatively or additionally, an impedance sensor may be used, configured for sensing a change in impedance of tissues provided between stimulators or/and electrodes, for example, correlative to a reaction to gastric contents or other substances. Optionally, alternatively or additionally, other sensor types may be used, including but not limited to a pressure sensor, a manometer, a moisture sensor, a temperature sensor, a motion sensor, a capacitance sensor and a mechanical sensor.

Additional details of structural and functional (operational) characteristics, properties, parameters, and technical features of exemplary embodiments of the system, and components thereof, for generating a distally traveling synthetic esophageal motion within a subject's esophagus, are as follows.

In exemplary embodiments, the elongated member is a medical intubation device, for example, a gastric feeding tube, such as a nasogastric or a nasojejunal intubation. In exemplary embodiments, the elongated member includes at least one sensor mounted or mountable on the elongated member. In exemplary embodiments, at least one sensor is mounted on the elongated member distally to a distal-most stimulator. In exemplary embodiments, the at least one sensor is, or includes, at least one of: a pH sensor, a pressure sensor, a manometer, an impedance sensor, a motion sensor, a capacitance sensor, and a mechanical sensor.

In exemplary embodiments, the series of stimulators is fixed to the elongated member. In exemplary embodiments, the series of stimulators includes an even number of bipolar electrode pairs in a range of between four bipolar electrode pairs and twenty bipolar electrode pairs. In exemplary embodiments, the bipolar electrodes pairs are distributable such that a proximal-most electrode pair is locatable proximally to the UES. In exemplary embodiments, the bipolar electrodes pairs are distributable such that a distal-most electrode pair is locatable distally to the LES.

In exemplary embodiments, the signal generator is an electrical signal generator capable of generating electrical signals, and sending (transmitting) such generated electrical signals to another component or device (apparatus) operatively (electrically/electronically) connected to the signal generator. In exemplary embodiments, the signal generator generates and sends the sequence of stimulating signals to the series of 'all' or 'some of' the stimulators, so as to evoke a plurality of local esophageal contractions in a form of a distally traveling synthetic esophageal motion along the esophageal length. In exemplary embodiments, the signal generator is operatively (electrically/electronically) connected to a control unit. In exemplary embodiments, the control unit is configured and operative for controlling the signal generator to produce the sequence of stimulating signals. In exemplary embodiments, the sequence of stimulating signals may be staggered in time, such that distally-located stimulators receive stimulating signals after more proximally-located stimulators. In exemplary embodiments, the control unit is configured and operative for controlling the signal generator to selectively transition the series of stimulators among three states of electrical connectivity. In exemplary embodiments, the three states correspond to: (i) the series of stimulators connected to the signal generator, (ii) the series of stimulators connected to ground, and (iii) the series of stimulators not connected to the signal generator.

In exemplary embodiments, the control unit is configured and operative for controlling the signal generator to generate the sequence of stimulating signals in a form of a plurality of electrical pulses. In exemplary embodiments, each of the electrical pulses has a pulse current in a range of between about 10 milliamperes and about 50 milliamperes, and a pulse duration in a range of between about 0.01 millisecond and about 0.5 millisecond. In exemplary embodiments, each of the electrical pulses has a pulse frequency in a range of between about 25 Hz and about 70 Hz. In exemplary embodiments, each of the electrical pulses is separated from an adjacent one of the electrical pulses by a time span of at least 0.5 second. In exemplary embodiments, the plurality of electrical pulses is produced as part of a plurality of electrical pulse trains, whereby each of the electrical pulse trains includes a number of electrical pulses. In exemplary embodiments, each of the electrical pulse trains has a train pulse duration in a range of between about 0.5 second and about 5 second. In exemplary embodiments, each of the electrical pulse trains is separated from an adjacent one of the electrical pulse trains by a separation time span having a range of between about 0.5 minute and about 60 minutes.

In exemplary embodiments, the sequence of stimulating signals includes at least one electrical pulse or electrical pulse train having a magnitude higher than a stimulating threshold between 5V and 20V. In exemplary embodiments, the signal generator is configured for developing local esophageal pressures of at least 40 mmHg for each of the local esophageal contractions.

In exemplary embodiments, the plurality of local esophageal contractions is in a form of a wave of distally progressing contractions within the esophagus. In exemplary embodiments, the wave of distally progressing contractions includes a second wave starting only after a first wave is finished, without overlapping of the second and first waves. In exemplary embodiments, the wave of distally progressing contractions includes a second wave beginning before a first wave completes travelling from upper portion of the esophagus. In exemplary embodiments, the system, and components thereof, are configured for generating the distally traveling synthetic esophageal motion wherein the esophagus exhibits characteristics of suspended esophageal peristaltic motility.

Herein illustratively described exemplary embodiments of a system for generating a distally traveling synthetic esophageal motion within a subject's esophagus may be implemented, for example, by a method for generating esophageal peristalsis in a patient intubated with a gastric tube, or/and for generating motility in other GI tract organs. In exemplary embodiments, such a method includes the following steps or procedures, not necessarily being limited to a particular order:

Positioning a plurality or series of stimulators, being, or including, at least two electrodes, with one or more proximally positioned electrodes and one or more distally positioned electrodes, at longitudinally spaced positions along the gastric tube, where the positions are selected such that after installation of the gastric tube, the at least two longitudinally spaced electrodes will be between the upper esophageal sphincter (UES) and the lower esophageal sphincter (LES).

Operatively, electrically connecting the series of stimulators, and the at least two electrodes thereof, to a signal generator.

Generating a sequence of stimulating signals, and sending (transmitting) the generated sequence of stimulating signals, for example, by the signal generator, to the series of stimulators. In exemplary embodiments, this step/procedure includes generating, and sending/transmitting to the series of stimulators, by the signal generator, a first stimulating signal at the proximally positioned electrode, thereby stimulating a proximal esophageal tissue. In exemplary embodiments, this step/procedure further includes generating, and sending (transmitting) to the series of stimulators, by the signal generator, a second stimulating signal at the distally positioned electrode, thereby stimulating a distal esophageal tissue.

In some embodiments, the electrodes apply electrical current in a series of one or more electrical pulse trains, wherein each electrical pulse train is composed of a series of cycles, and each cycle includes one electrical pulse. Each electrical pulse has an amplitude; in exemplary embodiments, the amplitude is higher than a stimulating threshold. In some embodiments, the stimulating threshold is between 5V and 20V, optionally, between 8V and 10V or between 10V and 15V; in other embodiments, the stimulating threshold may be higher or lower than these values. Each electrical pulse is provided for a duration of time. In some embodiments, the electrical pulse width (i.e., the duration) is equal to or greater than 5 milliseconds, and optionally, equal to or greater than 10 milliseconds. The applied electrical pulse is followed by a duration of lower current or/and no current. Together, one electrical pulse and one duration of low current compose a cycle. In some embodiments, one cycle lasts 20 ms; in other embodiments, one cycle lasts 15 ms, or optionally, 30 ms, or less than, greater than, or intermediate to these values. In some embodiments, multiple cycles are provided successively such that together the cycles form an electrical pulse train having a duration of one to two seconds. In other embodiments, electrical pulse trains are provided that are longer or shorter in duration. The electrical pulse train is then followed by a duration of no current or low current produced by below-threshold voltages.

In some embodiments, the sequence of electrical pulse trains or other signal sequence synthetically produces a wave of contractions (i.e., distally progressing synthetic esophageal contractions) that travels a length along the esophagus. In some embodiments, the contractions simulate (mimic) natural peristalsis. In some embodiments, a contractions wave in the esophagus initiates at least minimal functionality in one or more other portions of the GI tract. In some such embodiments, contractions continue to travel as a wave distally through the stomach and through at least a portion of the small intestine. In some embodiments, the wave of contractions evokes activity in the large intestine. In other embodiments, the contraction wave in the esophagus induces remote contractions in the lower GI tract, such as, for example, contractions within the duodenum, jejunum, ileum, caecum, colon, or/and rectum.

In some embodiments, before each electrical pulse or electrical pulse train, one or more below-threshold electrical pulses is/are applied to the tissue to prime the tissue and induce it to contract more firmly and efficiently and to begin contracting at lower voltage stimulation levels. Optionally, a preliminary, below-threshold electrical pulse train is applied before each stimulating electrical pulse or electrical pulse train. In some embodiments, a continuous below-threshold electrical pulse train is applied to specific portions of the esophagus to desensitize, and thereby avoid unneeded contractions within, the portions. For example, the LES must be open in order for material to pass from the esophagus into the stomach. In one embodiment therefore, one or more electrodes may also be positioned on the gastric tube such that after installation they are adjacent the LES to provide a continuous below-threshold electrical pulse train which will be applied to the LES to desensitize it so that it does not contract when material arrives. Such electrode(s) may also be used to close the LES if that is a desired response under some circumstances.

For purposes of further understanding exemplary embodiments of the present invention, in the following illustrative description thereof, reference is made to the figures. It is to be understood that the invention is not necessarily limited in its application to particular details of construction or/and arrangement of exemplary system components set forth in the following illustrative description. The invention is capable of other exemplary embodiments or of being practiced or carried out in various ways.

FIG. 1A schematically illustrates an exemplary system 10 including an elongated member 11 positioned in a patient's esophagus and including a plurality or series of stimulators 12, in accordance with some embodiments. In exemplary embodiments, the stimulators 12 are mounted or mountable on the elongated member 11 and distributed along a length thereof. The series of stimulators 12 is configured for stimulating a series of portions of the esophagus along an esophageal length spanning between the esophagus LES and UES.

Elongated member 11 may be any plastic or elastic rod or tube sized to enter and be pushed through the esophagus, for example, with no injury to adjacent tissues. Elongated member may be a probe, a catheter or/and a nasogastric tube (NGT); the latter is used, for example, for injecting food directly to a patient's stomach or/and pumping out chyme to relieve excessive gastric pressure. Stimulators 12 may be any mechanical, electrical or chemical local muscle or neural stimulators. Four stimulators 12 are shown for illustrative purposes, although any other number of stimulators may be provided. In exemplary embodiments, stimulators 12 are, or include, at least two longitudinally spaced electrodes, chargeable to opposite polarities. In exemplary embodiments, each stimulator 12 represents a number of electrodes (e.g., a terminal), for example, provided around a local periphery of elongated member 11. In exemplary embodiments, stimulators 12 are provided in a sequential (serial) order, for example, having a constant or selectively changeable distance therebetween. In exemplary embodiments, stimulators 12 include bipolar electrodes so that pairs of adjacent non-short-circuited electrodes can be used for closing an electrical circuit and thereby stimulate an esophageal muscle tissue in-contact and in-between the two electrodes.

A generator 13, for example, an electrical signal generator, is shown operatively (electrically) connected to stimulators 12 via elongated member 11, for example, over and along its outer periphery or via a lumen thereof. To synthetically produce a plurality of local esophageal contractions in a form of a distally traveling synthetic esophageal motion along a length of the esophagus, in accordance with a chosen scheme or logic, for example, such as for synthetically simulating or mimicking a naturally occurring esophageal peristalsis, separate generator outputs may be provided to respective separate electrodes or electrode groups 12. In exemplary embodiments, the spacing between electrodes or electrode groups 12 is less than 5 cm, and the distance between the most proximal electrode or electrode group 12 and most distal electrode or electrode group 12 is at least 10 cm. Such particular electrode configuration and spacing enables attaining sequential stimulation of the electrodes or electrode groups 12 along a significant portion or length of the esophagus between the UES and the LES. In exemplary embodiments, the signal generator 13 generates and sends the sequence of stimulating signals to the series of 'all' or 'some of' the stimulators 12, so as to evoke the plurality of local esophageal contractions in a form of a distally traveling synthetic esophageal motion along the esophageal length.

Figure 1B:
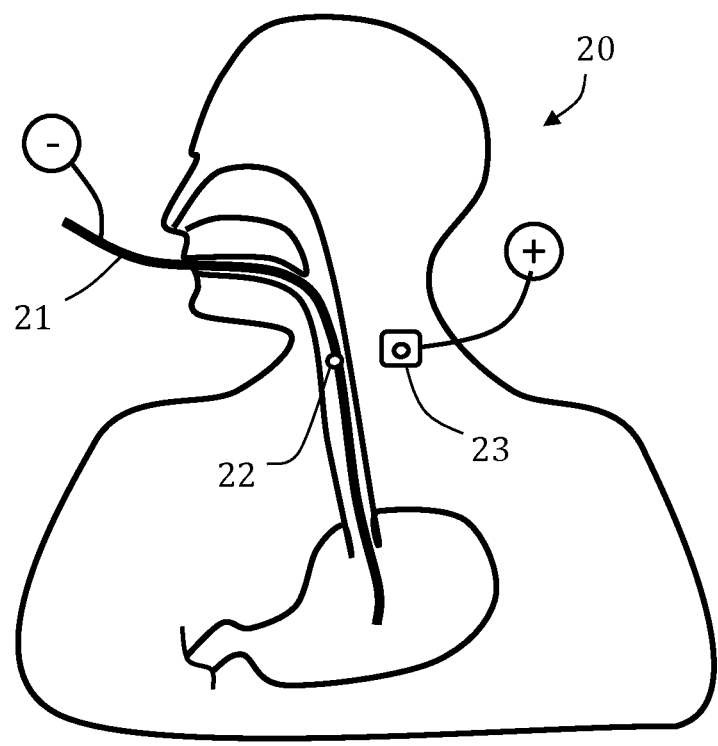
FIG. 1B schematically illustrates an exemplary oral feeding tube positioned in a patient's esophagus and including a mono-polar stimulator, in accordance with some embodiments of the invention.

In FIG. 1B, an exemplary system 20 is schematically illustrated including an elongated member in a form of an oral feeding tube 21 positioned in a patient's esophagus and including a mono-polar stimulator 22, in accordance with some embodiments. Although it is commonly more safe and convenient to place an esophageal intubation via a nasal cavity, there might be circumstances (e.g., with infant patients) where a tube is inserted via the oral cavity as suggested in this figure. Mono-polar stimulator 22 is electrically connected to an outside source or ground (shown in the figure as "(-)") and is selectively capable of closing an electrical circuit with an external electrode 23, for example, positioned on the patient's neck skin. A single electrode may be used to stimulate a neutrally sensitive region thereby evoking an esophageal contraction wave from the stimulated region and downward, for example, to the LES or the stomach interim. Optionally, alternatively or additionally, a single electrode may be used for local muscle contraction in order to serve as a barrier for refluxed gastric contents or/and for decreasing overall esophagus volume and increasing esophageal pressure, or/and optionally, evoking motility in other GI tract organs.

Figure 1C:
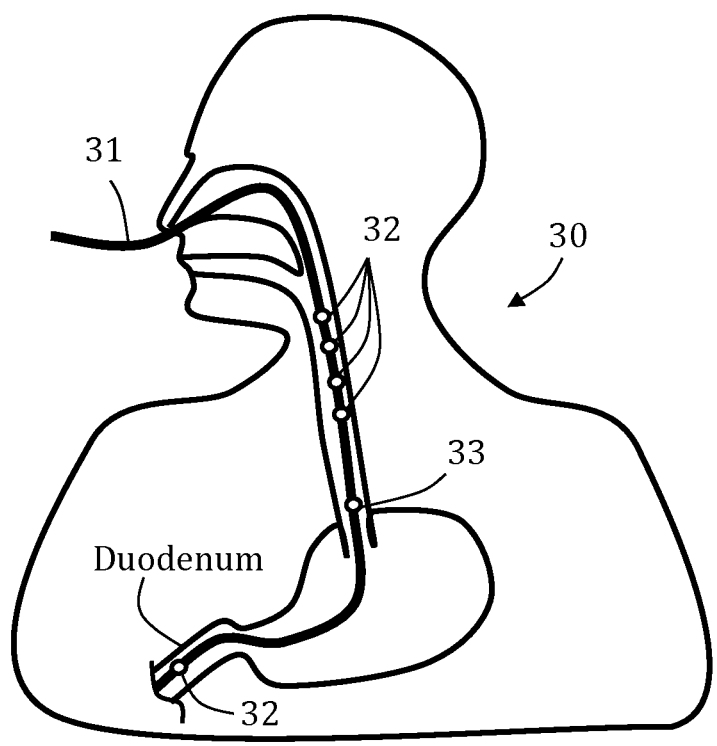
FIG. 1C schematically illustrates an exemplary feeding tube positioned in a patient's esophagus and including a plurality (series) of stimulators and a sensor, in accordance with some embodiments of the invention.

In FIG. 1C, an exemplary system 30 is schematically illustrated including an elongated member in a form of a feeding tube 31 positioned in a patient's esophagus and including a plurality or series of stimulators 32, and further including a sensor 33, in accordance with some embodiments. In exemplary embodiments, the stimulators 12 are mounted or mountable on the elongated member (feeding tube) 31 and distributed along a length thereof. The series of stimulators 32 is configured for stimulating a series of portions of the esophagus along an esophageal length spanning between the esophagus LES and UES.

Feeding tube 31 may be used to introduce partly digested food or fluids directly to the small intestine (e.g., opened at the duodenum or at the jejunum). In some embodiments, the stimulators 32 are positioned on the feeding tube 31 such that, when the feeding tube 31 is in place within a patient, the stimulators 32 are located within the esophagus, the stomach, the small intestine, or any combination thereof. For example, in FIG. 1C, the stimulators 32 are positioned in the esophagus, and also in the duodenum of the small intestine. The series of stimulators 32 includes at least two longitudinally spaced electrodes, chargeable to opposite polarities. In some embodiments, the individual stimulators are positioned regularly along the length of the feeding tube 31. For example, in one embodiment, a stimulator or stimulator pair is positioned every 4 cm along the feeding tube 31, allowing for multi-location stimulation within multiple GI organs.

In system 30 shown in FIG. 1C, the sensor 33 may be a pH sensor, for example, positioned adjacent or proximal to the LES or stomach entry. In the case of a substantially low pH, such as in the presence of acid refluxed chyme, sensor 33 automatically signals or/and initiates the stimulations protocol for electrodes 32 to force the gastric content to flow back towards the stomach. In cases where no sensor is present, different stimulation protocols may apply, for example continuous stimulation regimes in which different electrodes are used sequentially to stimulate local tissues at specific frequencies and magnitudes. Optionally, alternatively or additionally, a local esophageal contraction or spasm is synthetically evoked, for any chosen duration, to act as a local physical barrier, thereby preventing or diminishing refluxed substance from passing therethrough. Such a synthetically generated local contraction/spasm may be singular or generated at different occasions or/and portions of the esophagus. Optionally, alternatively or additionally, at least one of the electrodes may be applied as sensors, for example, as bio-impedance type sensors.

In exemplary embodiments, system 30 includes a signal generator, for example, similar to electrical signal generator 13 illustratively described above and shown in FIG. 1A. The signal generator 13 is operatively (electrically) connected to the series of stimulators 32, and the electrodes thereof, via feeding tube 31, for example, over and along its outer periphery or via a lumen thereof. In exemplary embodiments, the signal generator 13 generates and sends the sequence of stimulating signals to the series of 'all' or 'some of' the stimulators 32, so as to evoke the plurality of local esophageal contractions in a form of a distally traveling synthetic esophageal motion along the esophageal length.

For each of the preceding illustratively described exemplary systems 10 (shown in FIG. 1A) and 30 (shown in FIG. 1C), in exemplary embodiments, the signal generator 13 is operatively connected to a control unit, for example, control unit 15 and operative (electrical/electronic) connection [dashed line]17 (as shown in FIG. 1A). In exemplary embodiments, the operatively (electrically/electronically) connected control unit 15 may be 'physically' separate from (e.g., located outside housing of) the signal generator 13, for example, as shown in FIG. 1A. Alternatively, the operatively (electrically/electronically) connected control unit 15 may be 'physically' part of (e.g., located inside housing of) the signal generator 13. In exemplary embodiments, the control unit 15 is configured and operative for controlling the signal generator 13 to produce and send the sequence of stimulating signals to the series of stimulators 32. In exemplary embodiments, the sequence of stimulating signals may be staggered in time, such that distally-located stimulators receive stimulating signals after more proximally-located stimulators. In exemplary embodiments, the control unit 15 is configured and operative for controlling the signal generator 13 to selectively transition the series of stimulators 12 (system 10, FIG. 1A) or stimulators 32 (system 30, FIG. 1C) among three states of electrical connectivity. In exemplary embodiments, the three states correspond to: (i) the series of stimulators 12 or 32 connected to the signal generator 13, (ii) the series of stimulators 12 or 32 connected to ground, and (iii) the series of stimulators 12 or 32 not connected to the signal generator 13.

Additionally, for each of the preceding illustratively described exemplary systems (i.e., system 10 shown in FIG. 1A, and system 30 shown in FIG. 1C), in exemplary embodiments, the control unit 15 is configured and operative for controlling the signal generator 13 to generate the sequence of stimulating signals in a form of a plurality of electrical pulses. In exemplary embodiments, each of the electrical pulses has a pulse current in a range of between about 10 milliamperes and about 50 milliamperes, and a pulse duration in a range of between about 0.01 millisecond and about 0.5 millisecond. In exemplary embodiments, each of the electrical pulses has a pulse frequency in a range of between about 25 Hz and about 70 Hz. In exemplary embodiments, each of the electrical pulses is separated from an adjacent one of the electrical pulses by a time span of at least 0.5 second. In exemplary embodiments, the plurality of electrical pulses is produced as part of a plurality of electrical pulse trains, whereby each of the electrical pulse trains includes a number of electrical pulses. In exemplary embodiments, each of the electrical pulse trains has a train pulse duration in a range of between about 0.5 second and about 5 second. In exemplary embodiments, each of the electrical pulse trains is separated from an adjacent one of the electrical pulse trains by a separation time span having a range of between about 0.5 minute and about 60 minutes. In exemplary embodiments, the sequence of stimulating signals includes at least one electrical pulse or electrical pulse train having a magnitude higher than a stimulating threshold between 5V and 20V. In exemplary embodiments, the signal generator 13 is configured for developing local esophageal pressures of at least 40 mmHg for each of the local esophageal contractions.

Figure 2A:
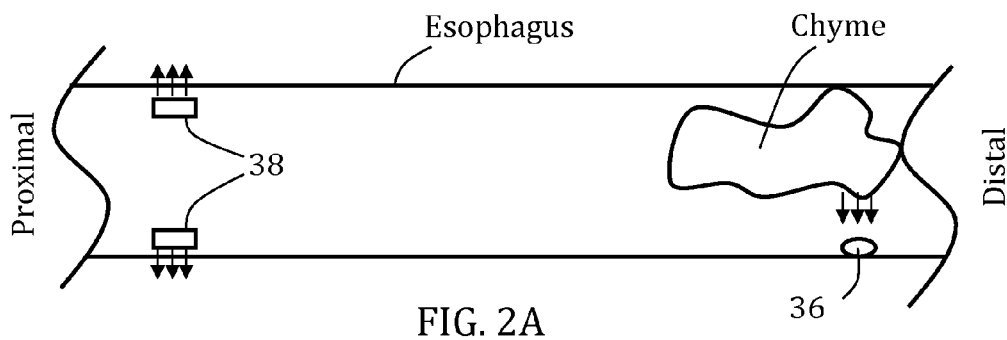
FIGS. 2A-2C schematically illustrate a partial cut view of a (synthetic) contraction wave stimulating system provided in an esophagus, shown at different operation stages, in accordance with some embodiments of the invention.
Figure 2B:
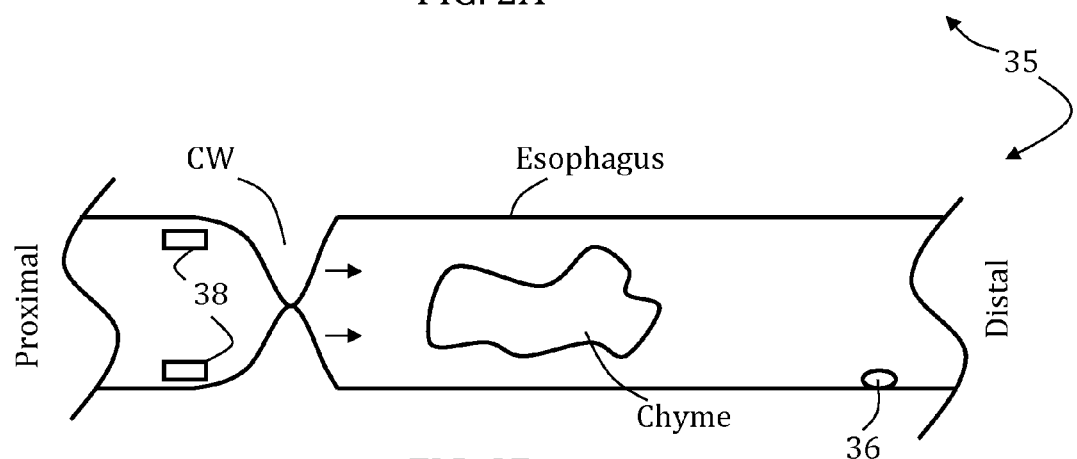
Figure 2C:
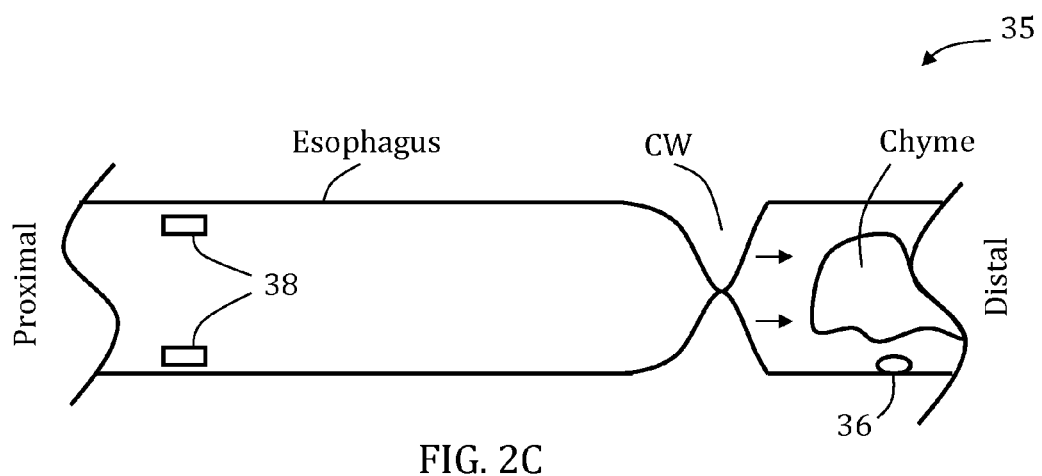
Figure 3B:
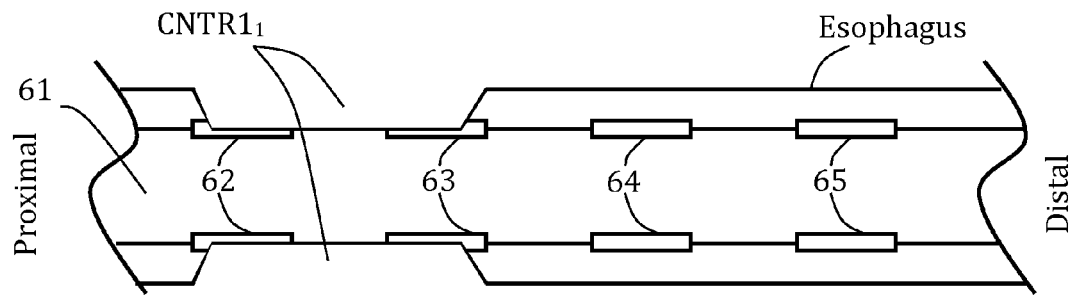
Figure 3C:
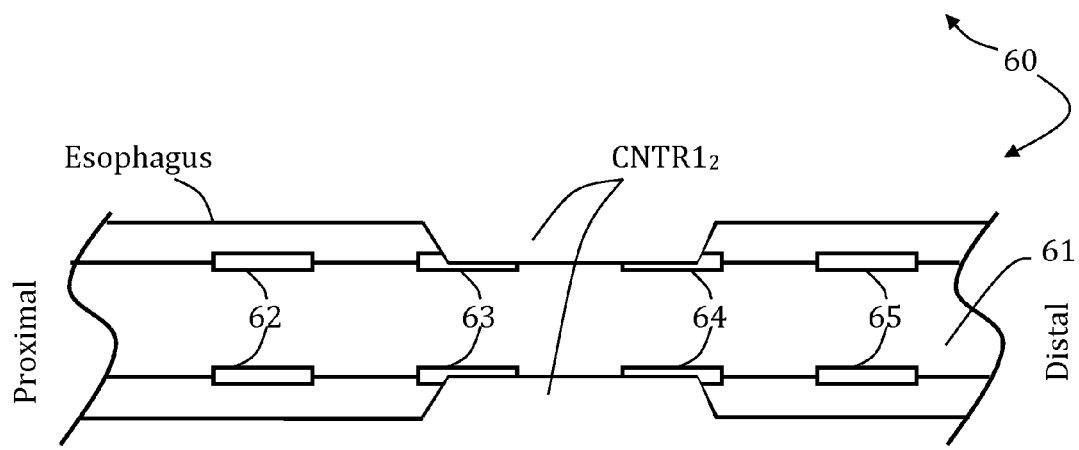
Figure 3D:
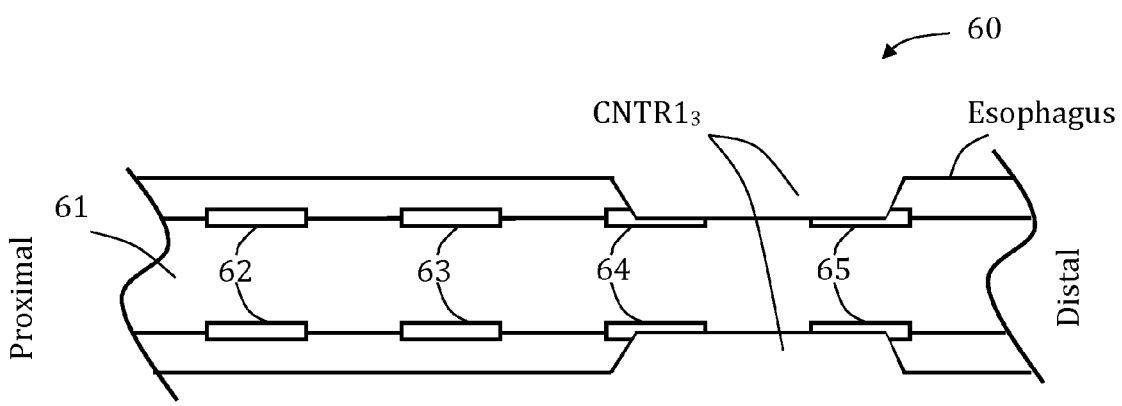
Figure 4B:
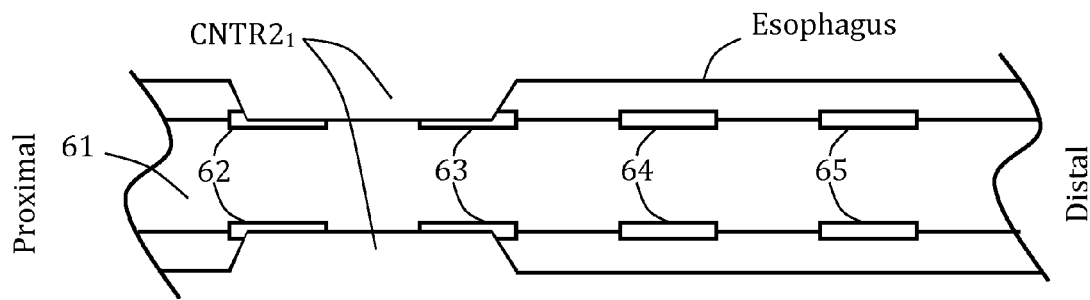
Figure 4C:
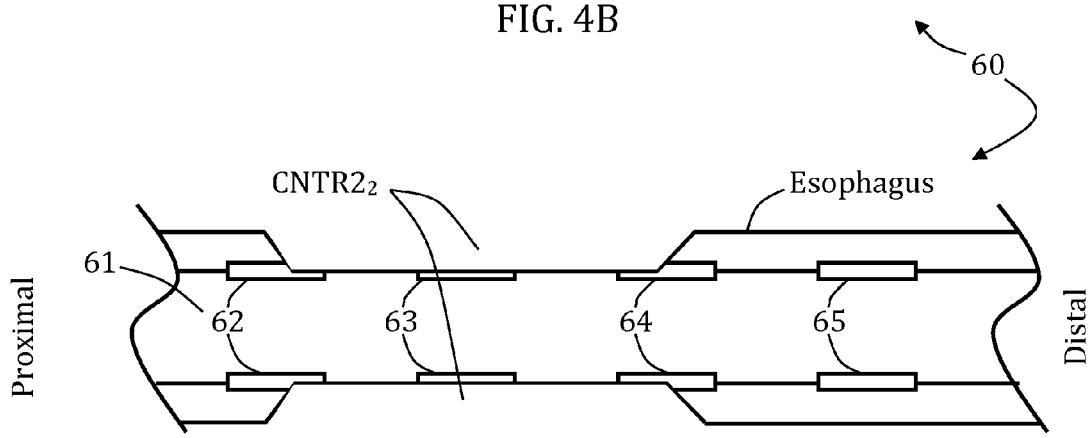
Figure 4D:
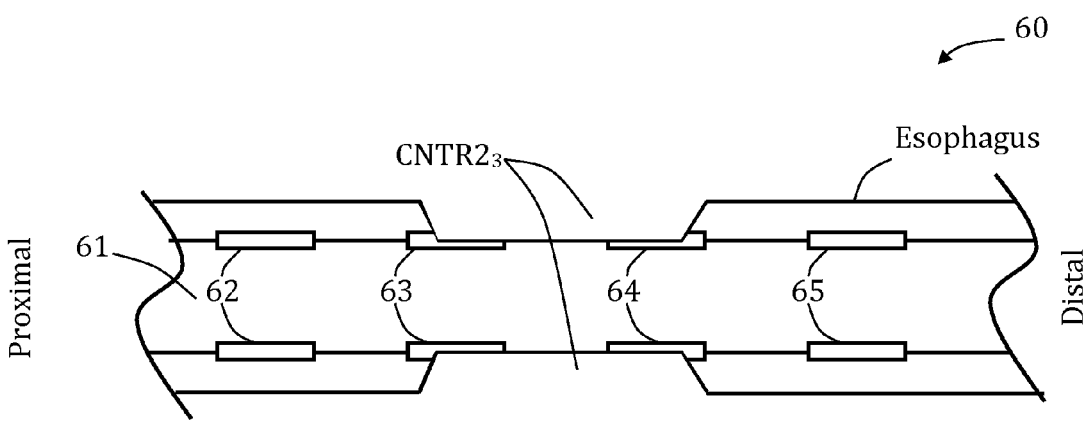
Figure 5A:
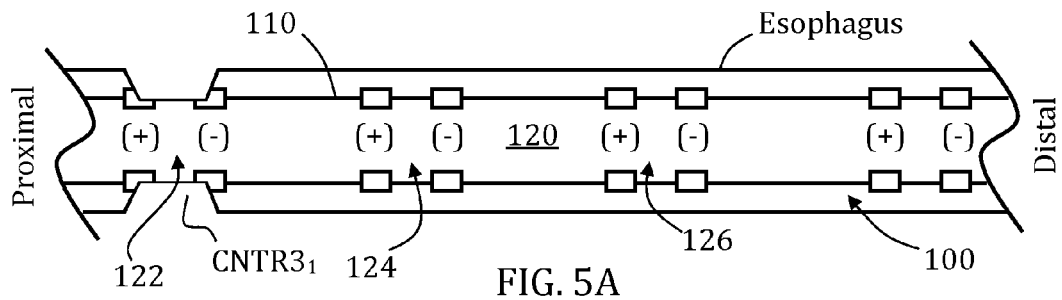
FIGS. 5A-5D schematically illustrate a third exemplary stimulation sequence and a correspondingly (synthetically) generated patterned esophageal motion, in accordance with some embodiments of the invention.
Figure 5B:
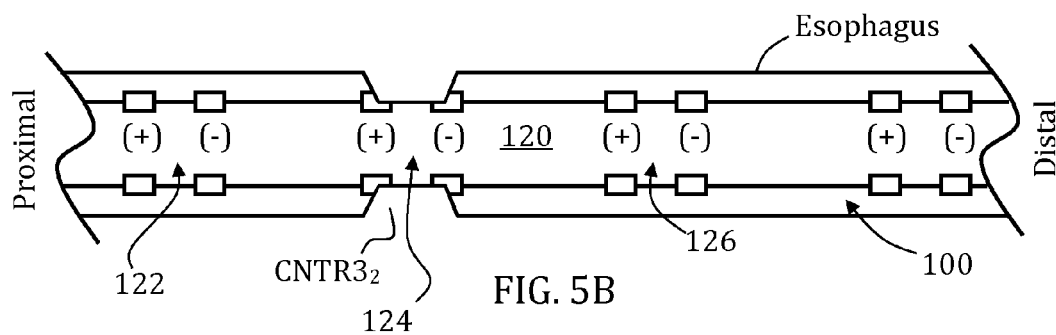
Figure 5C:
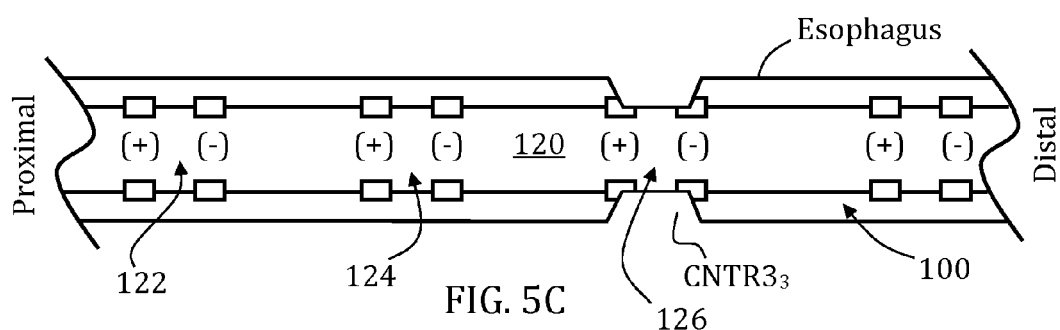
Figure 5D:
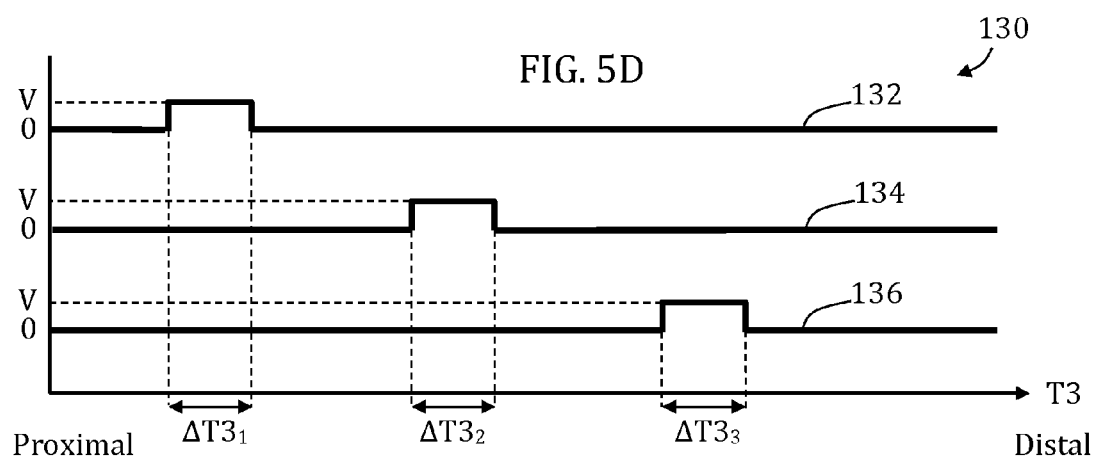

Reference is now made to FIGS. 2A-2C which schematically illustrate a partial cut view of a contractions wave stimulating system 35 provided in an esophagus, shown at different operation stages, in accordance with some embodiments. As shown in FIG. 2A, in one embodiment, a gastric content or chyme travels proximally away from the stomach adjacent to a pH sensor 36 previously deployed in the esophagus. Once a pH change is sensed, proximally positioned stimulators 38 initiate a stimulation having a magnitude or/and frequency adapted to synthetically evoke a plurality of local esophageal contractions in a form of a distally traveling and advancing synthetic type of (i.e., synthetically produced) esophageal motion (contractions wave) capable of pushing back the chyme. As shown in FIGS. 2B and 2C, a contractions wave CW is synthetically created by adjacent stimulators 38 and moves distally while pushing the chyme back towards the stomach. In exemplary embodiments, synthetically produced CW simulates (mimics) a naturally occurring esophageal peristalsis, although the synthesized motion may be different from natural peristalsis in at least one factor, for example, in magnitude, speed or/and frequency.

Reference is now made to FIGS. 3A-3D which schematically illustrate a first exemplary stimulation sequence or protocol 40 and a correspondingly synthetically generated patterned esophageal motion, using a stimulation system 60, in accordance with some embodiments. System 60 includes an elongated member in a form of a catheter 61 extending across a length in the esophagus, and a plurality or series of stimulators mounted on the elongated member (catheter) 61 and distributed along a length thereof. The plurality or series of stimulators is configured for stimulating a series of portions of the esophagus along an esophageal length spanning between the esophagus LES and UES, and includes at least two longitudinally spaced electrodes, chargeable to opposite polarities. For example, as shown in FIGS. 3A-3D, the plurality or series of stimulators includes four longitudinally spaced bipolar stimulation electrodes, chargeable to opposite polarities, including, for example, a proximal-most bipolar electrode 62, then bipolar electrode 63, bipolar electrode 64, and bipolar electrode 65. In this embodiment, each bipolar electrode encircles the catheter 61.

In exemplary embodiments, system 60 includes a signal generator, for example, electrical signal generator 13 illustratively described above and shown in FIG. 1A. The signal generator 13 is operatively (electrically) connectable to the bipolar stimulation electrode pairs via catheter 61, for example, over and along its outer periphery or via a lumen thereof. In exemplary embodiments, the signal generator 13 generates and sends the sequence of stimulating signals to the series of 'all' or 'some of' the stimulators, so as to evoke the plurality of local esophageal contractions in a form of a distally traveling synthetic esophageal motion along the esophageal length.

In exemplary embodiments, in system 60, the signal generator 13 is operatively (electrically/electronically) connected to a control unit, which is configured and operative in a same or similar manner as control unit 15 illustratively described hereinabove regarding implementation of exemplary systems 10 and 30 shown in FIGS. 1A and 1C, respectively. In such exemplary embodiments, the control unit 15 is configured and operative for controlling the signal generator 13 to generate the sequence of stimulating signals in a form of a plurality of electrical pulses, and, optionally, as electrical pulse trains.

Via operation of the signal generator 13, and optionally, an operatively connected control unit, such as control unit 15, the stimulation sequence or protocol 40 is implemented for generating and sending a combination of signals through different channels. Such generating and sending of a combination of signals through different channels includes, for example, a channel 42 adapted to stimulate an esophageal muscle tissue provided between electrodes 62 and 63, a channel 44 adapted to stimulate an esophageal muscle tissue provided between electrodes 63 and 64, and a channel 46 adapted to stimulate an esophageal muscle tissue provided between electrodes 64 and 65. As shown, channel 42 stimulates the esophagus with voltage V at duration $\Delta T1_1$ thus synthetically evoking a local contraction $CNTR1_1$ optionally as part of a distally traveling synthetic esophageal motion along a portion of an esophageal length, at the same duration. Immediately following, channel 44 stimulates the esophagus with voltage V at duration $\Delta T1_2$ thus synthetically evoking a second local contraction $CNTR1_2$ optionally as part of a distally traveling synthetic esophageal motion along another portion of the esophageal length, at the same duration. This is followed by stimulation through channel 46 with voltage V at duration $\Delta T1_3$, which synthetically evokes a third local contraction $CNTR1_3$ optionally as part of a distally traveling synthetic esophageal motion along another portion of the esophageal length, at the same duration.

FIGS. 4A-4D schematically illustrate a second exemplary stimulation sequence or protocol 50 and a correspondingly synthetically generated patterned esophageal motion, also using stimulation system 60, in accordance with some embodiments. Instead of only one channel (for example, channel 42), in exemplary embodiments, for example, as shown in FIGS. 4A-4D, system 60 operates with two channels. 52 and 54, with corresponding stimulation durations $\Delta T2_1$ and $\Delta T2_3$ that are overlapping at partial duration $\Delta T2_2$. This way, a synthetically produced traveling contractions wave synthetically simulates (mimics) a general peristaltic motion in which a first local contraction $CNTR2_1$, optionally as part of a distally traveling synthetic esophageal motion along a portion of the esophageal length, extends distally to become $CNTR2_2$, optionally as part of a distally traveling synthetic esophageal motion along another portion of the esophageal length, and only afterwards diminishes to leave a distal local contraction $CNTR2_3$, optionally as part of a distally traveling synthetic esophageal motion along another portion of the esophageal length.

FIGS. 5A-5D schematically illustrate a third exemplary stimulation sequence or protocol 130 and a correspondingly synthetically generated patterned esophageal motion using a system 100 for synthetically evoking motility in a GI tract portion, in accordance with some embodiments. As shown, system 100 includes an elongated member 110 (e.g., a tubular portion such as of a feeding tube) extending across a length in the esophagus. System 100 also includes a plurality or series of stimulators mounted on the elongated member 110 and distributed along a length thereof. The plurality or series of stimulators is configured for stimulating a series of portions of the esophagus along an esophageal length spanning between the esophagus LES and UES, and includes a plurality of longitudinally spaced electrodes 120, chargeable to opposite polarities. The electrodes 120 are arranged as a plurality of bipolar stimulation electrode pairs, including a proximal-most bipolar electrode pair 122, then bipolar electrode pair 124, and bipolar electrode pair 126. In some embodiments, the distance between each electrode in an electrode pair (i.e., a pair length, or a terminal width) is similar to, or the same as, the distance between each adjacent electrode pairs, such that all electrodes 120 are substantially evenly spaced. In such exemplary embodiments, the distance between each adjacent electrode is, for example, at least about 5 mm, optionally, at least about 10 mm, optionally, at least about 20 mm, optionally, at least about 30 mm, and optionally, at least about 50 mm. In the embodiment shown, each electrode encircles the catheter. Optionally and alternatively, the length of each electrode pair is substantially different (for example, shorter) than the distance between each adjacent electrode pairs. In some such embodiments, the length of each electrode pair is at most about 5 mm, optionally, at most about 10 mm, optionally, at most about 20 mm, whereas the distance between each adjacent electrode pairs is at least about 10 mm, optionally, at least about 20 mm, and optionally, at least about 30 mm, respectively.

In exemplary embodiments, system 100 includes a signal generator, for example, electrical signal generator 13 illustratively described above and shown in FIG. 1A. The signal generator 13 is operatively (electrically) connectable to the bipolar stimulation electrode pairs via elongated member 110, for example, over and along its outer periphery or via a lumen thereof. In exemplary embodiments, the signal generator 13 generates and sends the sequence of stimulating signals to the series of 'all' or 'some of' the stimulators, so as to evoke the plurality of local esophageal contractions in a form of a distally traveling synthetic esophageal motion along the esophageal length. In exemplary embodiments, in system 100, the signal generator 13 is operatively (electrically/electronically) connected to, a control unit, which is configured and operative in a same or similar manner as control unit 15 illustratively described hereinabove regarding implementation of exemplary systems 10, 30, and 60. In such exemplary embodiments, the control unit 15 is configured and operative for controlling the signal generator 13 to generate the sequence of stimulating signals in a form of a plurality of electrical pulses, and, optionally, electrical pulse trains.

Via operation of the signal generator 13, and optionally, an operatively connected control unit, such as control unit 15, the stimulation sequence or protocol 130 is implemented for generating and sending a combination of signals through different channels. Such generating and sending of a combination of signals through different channels includes, for example, a channel 132 adapted to stimulate an esophageal muscle tissue provided between electrodes pair 122, a channel 134 adapted to stimulate an esophageal muscle tissue provided between electrodes pair 124, and a channel 136 adapted to stimulate an esophageal muscle tissue provided between electrodes pair 126. As shown, channel 132 stimulates a first esophagus portion with voltage V at duration $\Delta T3_1$ thus synthetically evoking a local contraction $CNTR3_1$, in a form of a distally traveling synthetic esophageal motion along a portion of the esophageal length. A first period afterwards, channel 134 stimulates a second esophagus portion with voltage V at duration $\Delta T3_2$ thus synthetically evoking a second local contraction $CNTR3_2$, in a form of a distally traveling synthetic esophageal motion along another portion of the esophageal length. A second period afterwards, channel 136 stimulates a third esophagus portion with voltage V at duration $\Delta T3_3$, which synthetically evokes a third local contraction $CNTR3_3$, in a form of a distally traveling synthetic esophageal motion along another portion of the esophageal length. In some embodiments, at least one of the first period and the second period is between 0.1 second and 2 second, optionally, equal or less than 0.5 second.

Figure 6A:
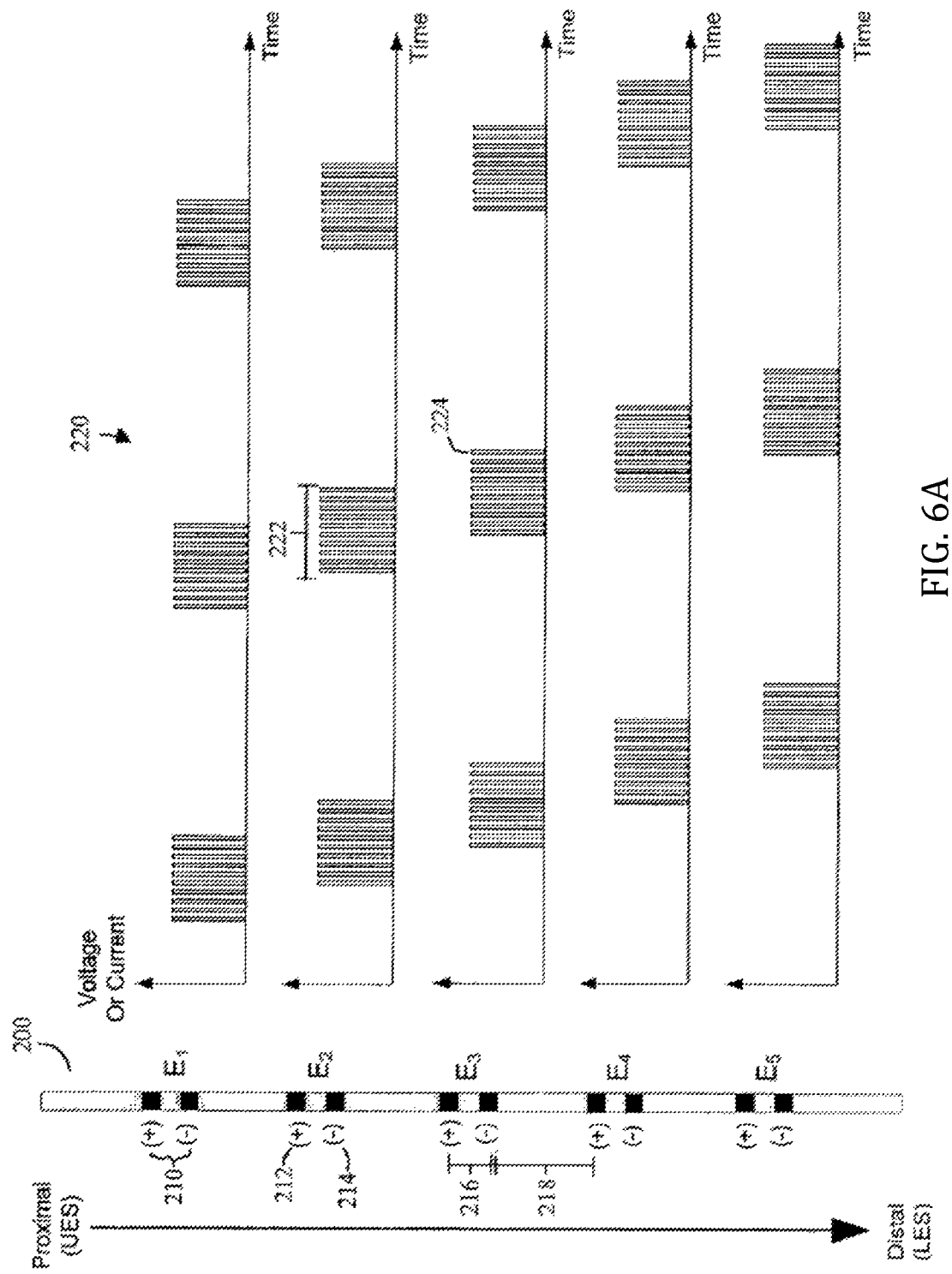
FIG. 6A schematically illustrates a top view of an exemplary esophageal intubation tube provided with a plurality (series) of stimulators, with each stimulator including two longitudinally spaced electrodes; an exemplary signal sequence from each terminal is also illustrated, in accordance with some embodiments of the invention.

FIG. 6A schematically illustrates an exemplary elongated member in a form of an esophageal intubation tube 200 configured for extending across a length in the esophagus and provided with a mounted plurality or series of stimulators (terminals) 210. The plurality or series of stimulators (terminals) 210 is configured for stimulating a series of portions of the esophagus along an esophageal length spanning between the esophagus LES and UES, and includes at least two longitudinally spaced electrodes, chargeable to opposite polarities: a positive electrode 212 and a negative (grounded) electrode 214, in accordance with some embodiments. The electrodes are spaced such that the distance 218 between each terminal is greater than the distance 216 between each electrode within any given terminal. As used herein, whenever a distance between electrodes is mentioned, the center to center distance is being referred to.

The electrodes 212 and 214 of each terminal 210 are operatively connectable, via esophageal intubation tube 200, for example, over and along its outer periphery or via a lumen thereof, to an electrical signal generator, for example, electrical signal generator 13 illustratively described above and shown in FIG. 1A. In exemplary embodiments, the signal generator 13 generates and sends the sequence of stimulating signals to the series of 'all' or 'some of' the stimulators, so as to evoke the plurality of local esophageal contractions in a form of a distally traveling synthetic esophageal motion along the esophageal length. In exemplary embodiments, the signal generator 13 is operatively (electrically/electronically) connected to a control unit, which is configured and operative in a same or similar manner as control unit 15 illustratively described hereinabove regarding implementation of exemplary systems 10, 30, 60, and 100. In such exemplary embodiments, the control unit 15 is configured and operative for controlling the signal generator 13 to generate the sequence of stimulating signals in a form of a plurality of electrical pulses, and, optionally, as electrical pulse trains.

Via operation of the signal generator 13, and optionally, an operatively connected control unit, such as control unit 15, a current or voltage, for example, a pulsed current or voltage, is provided to the positive electrode 212. An exemplary signal sequence or protocol 220 is also illustrated in FIG. 6A. As shown, an electrical pulse train 222 of electrical pulses 224 is provided to each terminal 210. In some embodiments, the signal sequence or protocol 220 is staggered in time such that distally-located terminals receive stimulating electrical pulse trains 222 after more proximally-located terminals. By providing a plurality of terminals 210 receiving staggered signal sequences, there is evoking a plurality of local esophageal contractions in a form of a distally traveling synthetic esophageal motion along the esophageal length, that simulates (mimics) a naturally occurring esophageal peristalsis. In the exemplary embodiment shown in FIG. 6A, there are three synthetically produced 'waves' of stimulations that distally progress down the esophagus with a second wave starting only after the first wave is finished (with no overlapping of the first and second waves).

Figure 6B:
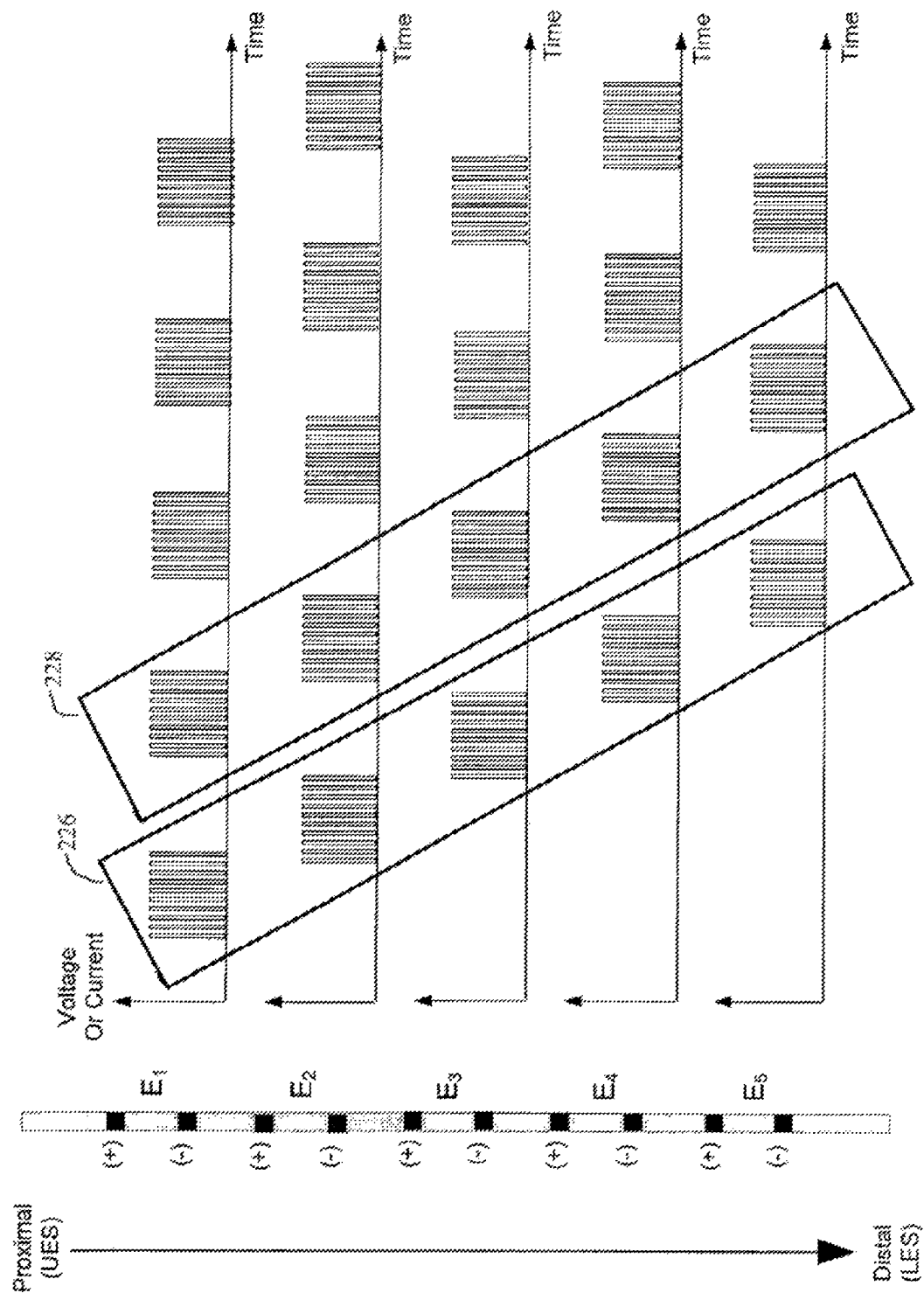
FIG. 6B schematically illustrates a top view of an exemplary esophageal intubation tube provided with a plurality (series) of stimulators, with each stimulator including two longitudinally spaced electrodes; an exemplary signal sequence from each terminal is also illustrated, in accordance with some embodiments of the invention.

A different approach is seen in FIG. 6B, where a second wave starting at the upper portion of the esophagus length begins before a previous wave of stimulations down the esophagus length is completed. In this exemplary implementation, there may be two distant esophagus length portions which contract at the same time. This may increase overall peristalsis efficacy, while better overcoming retrograding material that managed to infiltrate through distal contractions/waves.

In some intubation tube embodiments, such as, for example, the esophageal intubation tube embodiment of FIG. 6B, the electrodes 252 are spaced uniformly along the length of the intubation tube 250. In some such embodiments, polarity alternates between each electrode 252, forming bipolar electrode pairs 254. For example, in FIG. 6B, there are five electrode pairs 254, and the distance between each electrode 252 within an electrode pair is equidistant to the distance between electrodes 252 of adjacent pairs.

In an additional embodiment of a stimulation sequence or protocol, as described with reference to the intubation tube 250 of FIG. 6B, stimulation originates in the proximal-most electrode pair $E_1$. Various stimulation sequences or protocols can be applied to the first electrode pair $E_1$. In some embodiments, application of various stimulation sequences progresses until adequate stimulation is achieved. In one such embodiment, adequate stimulation is defined as a localized contraction of 40 mmHg. In other embodiments, adequate stimulation is selected from the range of 20 mmHg to 80 mmHg, and may equal any sub-range or individual value within this range. Once adequate stimulation is achieved with a given stimulation sequence, that stimulation sequence becomes fixed and is repeatedly applied to the first electrode pair. In some embodiments, the same process of applying various stimulation sequences is then performed with the next electrode pair $E_2$ until adequate stimulation is achieved. The same process may progress to each subsequent electrode pair in a similar fashion until adequate stimulation is achieved at each pair. In some embodiments, such a method of stimulation achieves a wave of contractions along the esophagus. In some embodiments, the wave induces contractions further along the GI tract, such as, for example, contractions within the stomach, small intestine, or/and large intestine.

Figure 7A:
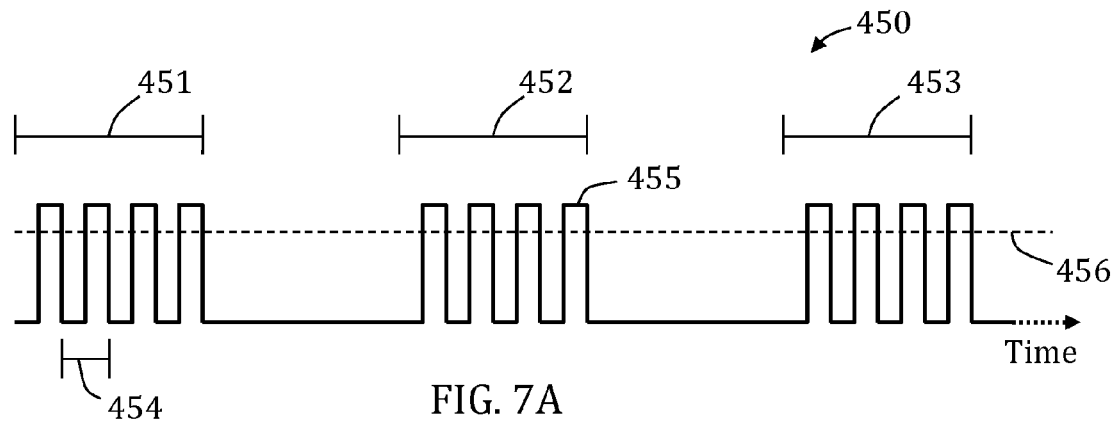
FIGS. 7A-7C schematically illustrates exemplary embodiments of different types of a series of electrical pulse trains, in accordance with some embodiments of the invention.
Figure 7B:
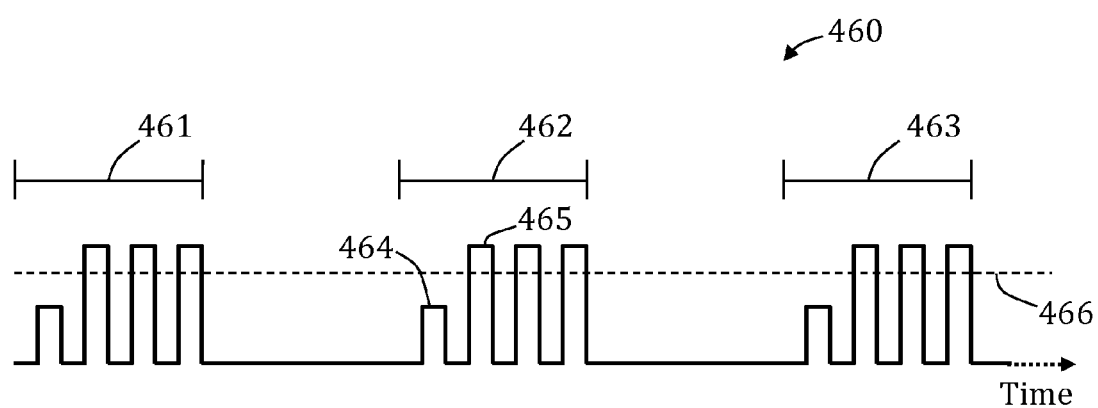
Figure 7C:
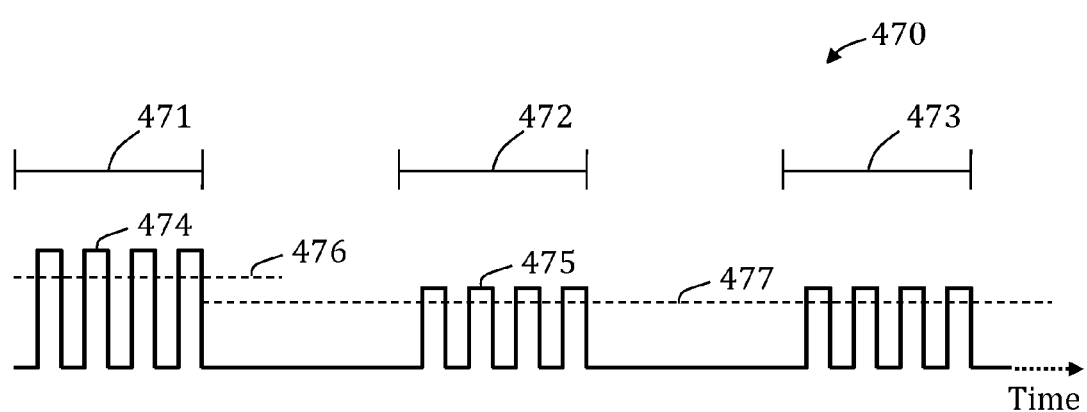

FIGS. 7A-7C schematically illustrate exemplary embodiments of different types of a series of electrical pulse trains 450, 460 and 470, respectively. Any of electrical pulse train series 450, 460 and 470, varies in time according to a chosen frequency and may be linked to at least one electrode terminal provided along a motility evoking system, such as any of the exemplary system embodiments (e.g., system 10, 30, 60, or 100) illustratively described hereinabove. Such exemplary embodiments may be implemented in a discrete manner, for example, whereby different stimulators (terminals) operate discretely in terms of electrical pulse train form, magnitude, or/and timing (frequency/duration).

In FIG. 7A, exemplary electrical pulse train series 450 shown includes at least three consecutive electrical pulse trains 451, 452, 453, each substantially same in form, magnitude, and frequency, for simplified illustrative purposes, although some variance may occur in normal practice. Each electrical pulse train includes a number of cycles, such as cycle 454 in electrical pulse train 451 (shown herein are four cycles in each electrical pulse train, for illustrative purposes), and each cycle includes a single electrical pulse, such as electrical pulse 455 in electrical pulse train 452. In exemplary embodiments, all cycles and electrical pulses therein are substantially the same in frequency and magnitude. As shown, at least these three electrical pulse trains are provided as part of a possible greater series of electrical pulse trains, whereby each electrical pulse train includes cycles of electrical pulses being greater in magnitude than a stimulation threshold 456 that is substantially constant, for example, as in some tissue portions along the GI tract, such as may occur in tissue portions of the esophagus along an esophageal length spanning between the esophagus LES and UES. Since each electrical pulse train exceeds threshold 456, local tissue in direct contact with or/and adjacent linked operative terminals will be subjected (when normally functional), for example, to a synthetically generated motility pattern, such as a synthetically generated plurality of local contractions (e.g., in case it includes a muscle tissue).

In FIG. 7B, exemplary electrical pulse train series 460 shown includes at least three consecutive electrical pulse trains 461, 462, 463, each substantially same in form, magnitude, and frequency, for simplified illustrative purposes, although some variance may occur in normal practice. Each electrical pulse train includes a number of cycles, and each cycle includes a single electrical pulse. In exemplary embodiments, each electrical pulse train includes a first cycle differing from its following cycles in at least magnitude of electrical pulse. As shown in this exemplary illustrative embodiment, in electrical pulse train 462, a first electrical pulse 464 is substantially smaller in magnitude than following electrical pulses (including electrical pulse 465). In some such embodiments, electrical pulse 464 is smaller in magnitude than a stimulation threshold 466 whereas electrical pulse 465 is substantially greater than threshold 466. At least in some tissue portions along the GI tract, such as in tissue portions of the esophagus along an esophageal length spanning between the esophagus LES and UES, one or more below-threshold electrical pulses can be applied to prime the tissue and synthetically induce the tissue to contract more firmly and efficiently and to begin contracting at lower voltage stimulation levels.

At least in some tissue portions along the GI tract, such as in tissue portions of the esophagus along an esophageal length spanning between the esophagus LES and UES, following at least one electrical pulse, optionally, at least one train of such electrical pulses, each electrical pulse or train of electrical pulses being substantially greater than a minimal local stimulation threshold, the minimal local threshold may drop so other following electrical pulses can be smaller in magnitude than the previous one(s), even if they are smaller than the original stimulation threshold, while still synthetically evoking local motility along the GI tract. In exemplary embodiments, for example, as applied to the esophagus, such synthetically evoked local motility corresponds to generating a distally traveling synthetic esophageal motion within the esophagus of a subject.

In FIG. 7C, exemplary electrical pulse train series 470 shown includes at least three consecutive electrical pulse trains 471, 472, 473, each substantially same in form and frequency, for simplified illustrative purposes, although some variance may occur in normal practice; yet differentiated in electrical pulse magnitudes. Each electrical pulse train includes a number of cycles, and each cycle includes a single electrical pulse. In exemplary embodiments, electrical pulse train 471 includes electrical pulses (including electrical pulse 474) which are substantially greater in magnitude than electrical pulses of consecutive electrical pulse trains 472 and 473 (including electrical pulse 475). In some such embodiments, electrical pulse 474 is greater in magnitude than a first stimulation threshold 476, whereas electrical pulse 475 is substantially smaller than first stimulation threshold 476, yet substantially greater than a second stimulation threshold 477.

In exemplary embodiments, different electrical pulse train series types, such as ones being similar to any of electrical pulse train series 450, 460 and 470, may be combined in any fashion as segments as part of a single continuous type of electrical pulse train series or as part of a consecutive type of electrical pulse train series, according to need or/and according to local anatomical function.

In some embodiments, only one or some heterogeneous electrical pulse trains (such as electrical pulse train 461 in series 460) may be needed and can be followed by more homogeneous electrical pulse trains (such as electrical pulse train 451 in series 450).

In some embodiments, in a heterogeneous series (such as electrical pulse train series 470), at least one electrical pulse train, for example, including at least one higher-magnitude electrical pulse train (such as electrical pulse train 471) or/and at least one lower-magnitude electrical pulse train (such as electrical pulse train 472), is heterogeneously formed (e.g., similar to electrical pulse train 461 in series 460), for example, including electrical pulses differentiated in magnitude.

In some embodiments, at least in some tissue portions along GI tract, such as in tissue portions of the esophagus along an esophageal length spanning between the esophagus LES and UES, stimulation threshold may vary continuously, either in response to previous local stimulation(s) or/and due to different, in-direct or irrelevant causes. In such exemplary embodiments, electrical pulse trains or/and electrical pulses may be changed accordingly, in order to achieve or/and maintain improved efficiency throughout operation of the motility evoking system. Stimulation threshold variance may be random or purposive (e.g., only via a drop in time under repetitive stimulations until possibly reaching a minimal asymptote).

In some embodiments, means (for example, one or more of a pressure sensor/detector, an electrical impedance sensor/detector, and a pH sensor/detector, for example, part of, or operatively connected to, the control unit) are provided with the motility evoking system which detect local conditions to asses and choose a specified localized stimulation magnitude accordingly. Local conditions may include, for example, pressure or/and impedance, which may be used in assessing or calculating a discrete minimal stimulation threshold; or/and, for example, pH, which may be used in assessing presence of retrograde gastric content. In exemplary embodiments, the motility evoking system may include one or more special purpose sensing elements, such as at least one sensor, for example, sensor 33, for example, as a pH sensor, as in the exemplary embodiment of system 30 shown in FIG. 1C). In exemplary embodiments, the motility evoking system may utilize at least some of its stimulators, and stimulation electrodes included therein, for sensing local conditions (such as by applying them for measuring impedance). In exemplary embodiments, the motility evoking system may be an open-loop type of system, in the sense the system (and electrical components thereof) are selectively or semi-automatically set by an operator according to need. In exemplary embodiments, the motility evoking system may be a closed-loop type of system, in the sense that the system (and electrical components thereof) are autonomously controlled by changing stimulation magnitudes or/and other parameters per measured or sensed conditions.

Figure 8:
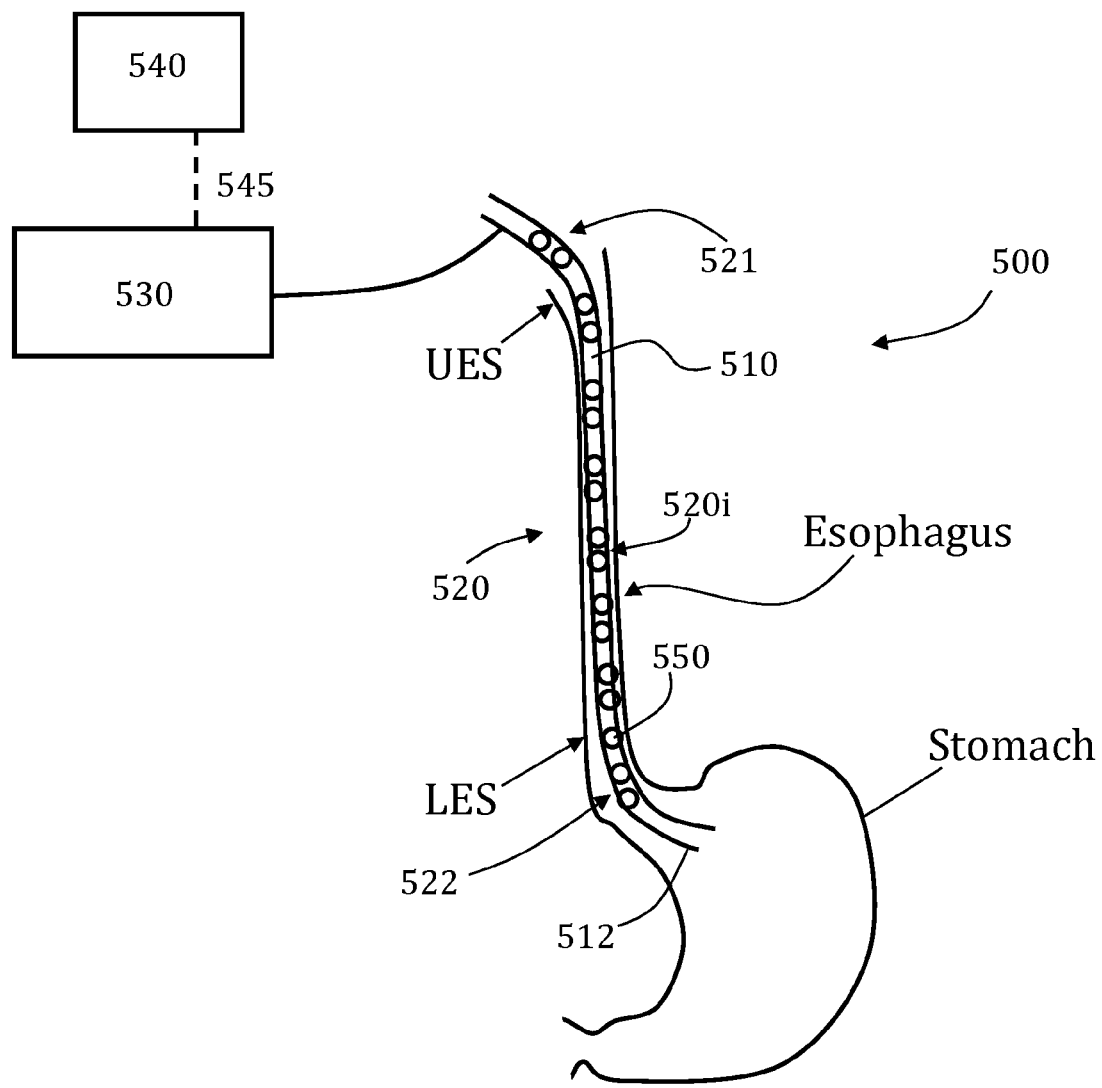
FIG. 8 schematically illustrates an exemplary system for generating a distally traveling synthetic esophageal motion within a subject's esophagus, in accordance with some embodiments of the invention.

Reference is now made to FIG. 8, which schematically illustrates an exemplary system 500 for generating a distally traveling synthetic esophageal motion within a subject's esophagus, in accordance with some embodiments of the invention. In exemplary embodiments, system 500 is configured for generating the distally traveling synthetic esophageal motion wherein the esophagus exhibits characteristics of suspended esophageal peristaltic motility. System 500 includes an elongated member 510 that is sized and configured for nasal or oral placement into the esophagus. Elongated member 510 is optionally a medical intubation device such as a gastric feeding tube having a distal end 512 optionally provided in the stomach following commonly practiced implantation. A series of stimulators 520 is mounted on (e.g., fixed to) the elongated member 510 and distributed along a length thereof. The series of stimulators 520 is configured for stimulating a series of portions 560 of the esophagus along an esophageal length spanning between the esophagus LES and UES. The series of stimulators 520 includes at least two longitudinally spaced electrodes (such as electrode pair 520i), chargeable to opposite polarities. In exemplary embodiments, the series of stimulators 520 may include an even number of bipolar electrode pairs in a range of between four bipolar electrode pairs and twenty bipolar electrode pairs, for example, six bipolar electrode pairs, or eight bipolar electrode pairs, or ten bipolar electrode pairs. In exemplary embodiments, the bipolar electrodes pairs are optionally distributable such that a proximal-most electrode pair 521 is locatable proximally to the UES or/and a distal-most electrode pair 522 is locatable distally to the LES.

Optionally, elongated member 510 includes at least one sensor 550 mounted or mountable thereon, optionally proximally (as shown) or distally to distal-most stimulator (e.g., distal-most electrode pair 522). Sensor 550 may include at least one of: a pH sensor, a pressure sensor, a manometer, an impedance sensor, a motion sensor, a capacitance sensor, and a mechanical sensor.

System 500 also includes a signal generator 530 that is configured for generating and sending a sequence of stimulating signals to the series of ('all' or 'some of') the stimulators 520, so as to evoke a plurality of local esophageal contractions in a form of a distally traveling synthetic esophageal motion along the esophageal length (between the UES and the LES). The plurality of local esophageal contractions may be in a form of a wave of distally progressing contractions within the esophagus. Such a wave of distally progressing contractions may include a second wave starting only after a first wave is finished, without overlapping of the second and first waves, or/and a second wave beginning before a first wave completes travelling from upper portion of the esophagus.

Signal generator 530 is optionally configured for developing local esophageal pressures of at least 40 mmHg for each of the local esophageal contractions, or optionally of at least 100 mmHg. In some embodiments, the sequence of stimulating signals includes at least one electrical pulse or electrical pulse train having a magnitude higher than a stimulating threshold in a range of between about 5V and about 20V, including, for example, a stimulating threshold in a range of between about 8V and about 10V, or a stimulating threshold in a range of between about 10V and about 15V, or a stimulating threshold in a range of between about 15V and about 20V.

Signal generator 530 is operatively (electrically/electronically) connected to a control unit, for example, control unit 540 and operative (electrical/electronic) connection [dashed line] 545 (as shown in FIG. 8). In exemplary embodiments, the operatively (electrically/electronically) connected control unit 540 may be 'physically' separate from (e.g., located outside) the signal generator 530, for example, as shown in FIG. 8. Alternatively, the operatively (electrically/electronically) connected control unit 540 may be 'physically' part of (e.g., located inside) the signal generator 530. In exemplary embodiments, the control unit 540 is configured and operative in a same or similar manner as control unit 15 illustratively described hereinabove regarding implementation of exemplary systems 10, 30, 60, and 100. In exemplary embodiments, the control unit 540 is configured and operative for controlling the signal generator 530 to produce the sequence of stimulating signals. In exemplary embodiments, the sequence of stimulating signals may be staggered in time, such that distally-located stimulators receive stimulating signals after more proximally-located stimulators. In exemplary embodiments, the control unit 540 is configured and operative for controlling the signal generator 530 to selectively transition the series of stimulators 520 among three states of electrical connectivity. In exemplary embodiments, the three states correspond to: (i) the series of stimulators 520 connected to the signal generator 530, (ii) the series of stimulators 520 connected to ground, and (iii) the series of stimulators 520 not connected to the signal generator 530.

In exemplary embodiments, control unit 540 is configured and operative for controlling the signal generator 530 to generate the sequence of stimulating signals in a form of a plurality of electrical pulses. In exemplary embodiments, each of the electrical pulses has a pulse current in a range of between about 10 milliamperes and about 50 milliamperes, and a pulse duration in a range of between about 0.01 millisecond and about 5 millisecond. In exemplary embodiments, the pulse current is in a range of between about 15 milliamperes and about 25 milliamperes, for example, a pulse current of about 20 milliamperes. In exemplary embodiments, the pulse duration is in a range of between about 0.1 millisecond and about 2 millisecond, or optionally between about 0.5 millisecond and about 1 millisecond, or optionally between about 0.8 millisecond and about 1 millisecond. Each of the electrical pulses may have a pulse frequency in a range of between about 25 Hz and about 150 Hz, including, for example, a range of between about 50 Hz and about 70 Hz. In exemplary embodiments, the pulse frequency is about 60 Hz. In exemplary embodiments, each of the electrical pulses may be separated from an adjacent one of the electrical pulses by a time span of at least about 0.5 second. The plurality of electrical pulses may be produced as part of a plurality of electrical pulse trains, whereby each of the electrical pulse trains may include a number of the electrical pulses, and whereby each of the electrical pulse trains has a train pulse duration in a range of between about 0.5 second and about 5 seconds, for example, a train pulse duration of about 1.5 seconds. Optionally, each of the electrical pulse trains is separated from an adjacent one of the electrical pulse trains by a separation time span having a range of between about 0.5 minute and about 60 minutes, including, for example, a separation time span of about 1 minute, or about 2 minutes, or about 5 minutes, or about 10 minutes.

In exemplary embodiments, the elongated member and the series of stimulators are system components that may be configured and operative together as a 'self-contained', 'stand-alone', and 'connectable' (linkable), device or apparatus, for example, as an implant, corresponding to a (structural/functional) sub-combination of exemplary embodiments of the herein disclosed system. In exemplary embodiments, such an implant is suitable for use, for example, as part of the herein disclosed system, in generating a distally traveling synthetic esophageal motion within a subject's esophagus. For example, such an implant is operatively [electrically/electronically] connectable (linkable) to a signal generator (for example, that is operatively connected to a control unit), thereby forming exemplary embodiments of a system for generating a distally traveling synthetic esophageal motion within a subject's esophagus.

Thus, according to an aspect of some embodiments of the invention, there is provided an implant for use in generating a distally traveling synthetic esophageal motion within a subject's esophagus. In exemplary embodiments, the implant includes: an elongated member sized and configured for nasal or oral placement into the esophagus; and a series of stimulators fixed to the elongated member and distributed along a length of the elongated member, wherein the series of stimulators is configured for stimulating a series of portions of the esophagus along an esophageal length spanning between the esophagus LES and UES, and includes at least two longitudinally spaced electrodes, chargeable to opposite polarities. In such exemplary embodiments of the implant, the elongated member is connectable to a signal generator configured for generating and sending a sequence of stimulating signals to the series of stimulators, so as to evoke a plurality of local esophageal contractions in a form of a distally traveling synthetic esophageal length. In such exemplary embodiments of the implant, and of the elongated member thereof, the series of (all or some of) the stimulators is configured and operative to receive the sequence of signals generated and sent by the signal generator, so as to be able to evoke the plurality of local esophageal contractions in a form of a distally traveling synthetic esophageal motion along the esophageal length, for example, between the UES and the LES.

Figure 9:
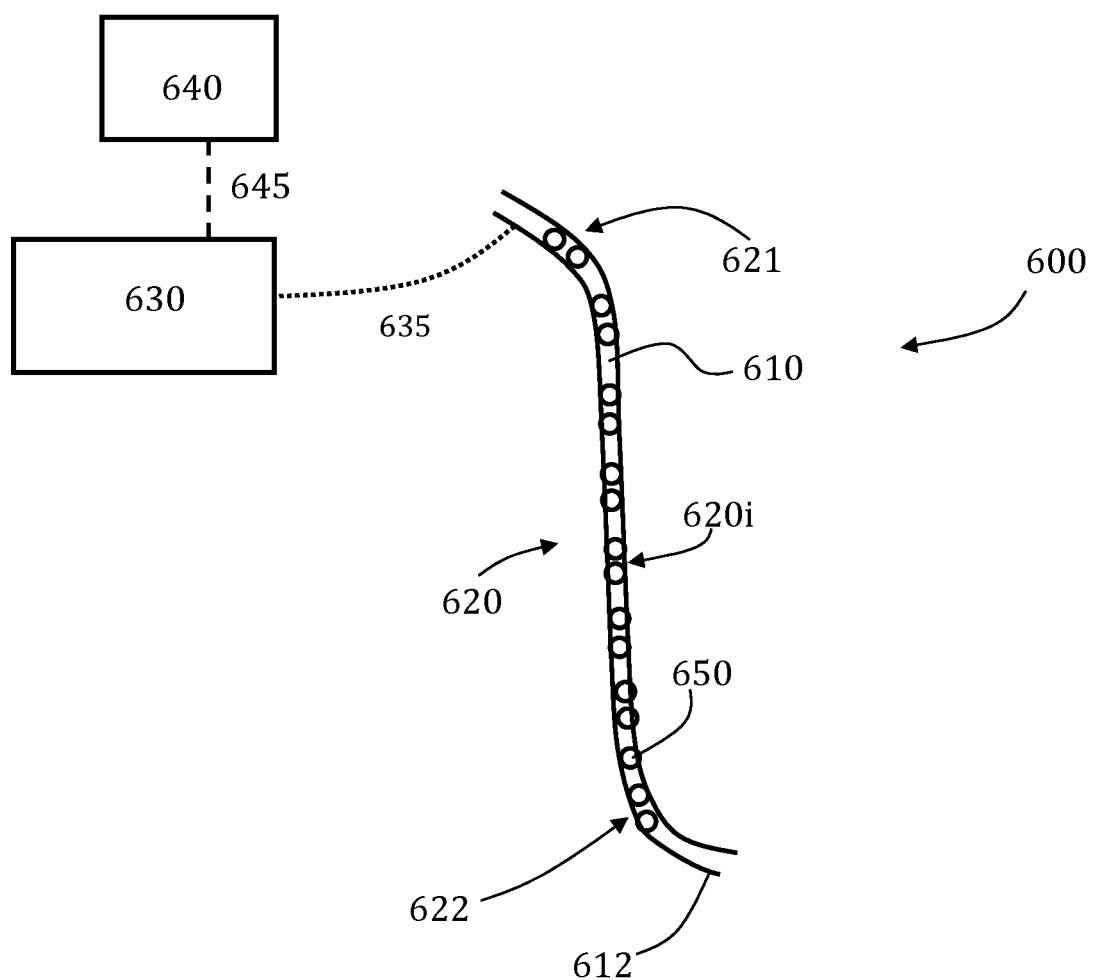
FIG. 9 schematically illustrates an exemplary implant suitable for use in generating a distally traveling synthetic esophageal motion within a subject's esophagus, in accordance with some embodiments of the invention.

FIG. 9 schematically illustrates an exemplary implant 600 suitable for use in generating a distally traveling synthetic esophageal motion within a subject's esophagus, in accordance with some embodiments of the invention. In exemplary embodiments, the implant 600 is configured and operative for being suitable for use in generating the distally traveling synthetic esophageal motion within a subject's esophagus wherein the esophagus exhibits different physiological conditions or/and characteristics, for example, wherein the esophagus exhibits characteristics of suspended esophageal peristaltic motility.

The implant 600 includes an elongated member 610 that is sized and configured for nasal or oral placement into the esophagus. In exemplary embodiments, elongated member 610 is a medical intubation device, such as a gastric feeding tube, having a distal end 612 optionally provided in the stomach following commonly practiced implantation. The implant 600 further includes a series of stimulators 620 fixed to the elongated member 610 and distributed along a length thereof. The series of stimulators 620 is configured for stimulating a series of portions of the esophagus along an esophageal length spanning between the esophagus LES and UES, and includes at least two longitudinally spaced electrodes (such as electrode pair 620*i*), chargeable to opposite polarities. In exemplary embodiments, the series of stimulators 620 may include an even number of bipolar electrode pairs in a range of between four bipolar electrode pairs and twenty bipolar electrode pairs, for example, six bipolar electrode pairs, or eight bipolar electrode pairs, or ten bipolar electrode pairs. In exemplary embodiments, the bipolar electrodes pairs are distributable in a manner such that a proximal-most electrode pair 621 is locatable proximally to the UES or/and a distal-most electrode pair 622 is locatable distally to the LES.

In exemplary embodiments, the elongated member 610 includes at least one sensor, for example, sensor 650, mounted or mountable thereon, optionally proximally (as shown) or distally to distal-most stimulator (e.g., distal-most electrode pair 622). In exemplary embodiments, the at least one sensor, for example, sensor 650, is or includes at least one of: a pH sensor, a pressure sensor, a manometer, an impedance sensor, a motion sensor, a capacitance sensor, and a mechanical sensor. For example, a pH sensor may be configured and operative for sensing a change (e.g., decrease) of local pH, for example, due to the presence of gastric contents proximally to the LES. For example, an impedance sensor may be configured and operative for sensing a change in impedance of tissues provided between stimulators or/and electrodes, for example, correlative to a reaction to gastric contents or other substances.

In exemplary embodiments of the implant 600, the elongated member 610 is configured in a manner so as to be operatively (electrically/electronically) connectable (linkable) to a signal generator, for example, signal generator 630. In FIG. 9, exemplary operative connectability is represented by the 'dotted line' 635. In such exemplary embodiments, and in exemplary embodiments wherein the elongated member 610 is operatively (electrically/electronically) connected (linked) [via operative connection 635] to the signal generator 630, the signal generator 630 is configured for generating and sending a sequence of stimulating signals to the series of (all or some of) the stimulators 620, so as to be able to evoke a plurality of local esophageal contractions in a form of a distally traveling synthetic esophageal motion along the esophageal length (for example, between the UES and the LES). Accordingly, in such exemplary embodiments of the implant 600, and of the elongated member 610, the series of (all or some of) the stimulators 620 is configured and operative to receive [via operative connection 635] the sequence of signals generated and sent by the signal generator 630, so as to be able to evoke the plurality of local esophageal contractions in a form of a distally traveling synthetic esophageal motion along the esophageal length (for example, between the UES and the LES). In such exemplary embodiments, the plurality of local esophageal contractions may be in a form of a wave of distally progressing contractions within the esophagus. Such a wave of distally progressing contractions may include a second wave starting only after a first wave is finished, without overlapping of the second and first waves, or/and a second wave beginning before a first wave completes travelling from upper portion of the esophagus.

In such exemplary embodiments, and in exemplary embodiments wherein the elongated member 610 is operatively (electrically/electronically) connected (linked) [via operative connection 635] to the signal generator 630, the signal generator 630 is configured for developing local esophageal pressures of at least 40 mmHg, or optionally, at least 100 mmHg, for each of the local esophageal contractions. In some embodiments, the sequence of stimulating signals includes at least one electrical pulse or electrical pulse train having a magnitude higher than a stimulating threshold in a range of between about 5V and about 20V, including, for example, a stimulating threshold in a range of between about 10V and about 15V, or a stimulating threshold in a range of between about 15V and about 20V.

In exemplary embodiments of the implant 600, wherein the elongated member 610 is operatively (electrically/electronically) connected (linked) [via operative connection 635] to the signal generator 630, the signal generator 630 is operatively connected to a control unit, for example control unit 640 and operative (electrical/electronic) connection [dashed line] 645 (as shown in FIG. 9). In such exemplary embodiments, the operatively (electrically/electronically) connected control unit 640 may be 'physically' separate from (e.g., located outside housing of) the signal generator 630, for example, as shown in FIG. 9. Alternatively, the operatively (electrically/electronically) connected control unit 640 may be 'physically' part of (e.g., located inside housing of) the signal generator 630. In exemplary embodiments, the control unit 640 is configured and operative for controlling the signal generator 630 to produce and send the sequence of stimulating signals to the series of stimulators 620. In exemplary embodiments, the sequence of stimulating signals may be staggered in time, such that distally-located stimulators receive stimulating signals after more proximally-located stimulators. In exemplary embodiments, the control unit 640 is configured and operative for controlling the signal generator 630 to selectively transition the series of stimulators 620 among three states of electrical connectivity. In exemplary embodiments, the three states correspond to: (i) the series of stimulators 620 connected to the signal generator 630, (ii) the series of stimulators 620 connected to ground, and (iii) the series of stimulators 620 not connected to the signal generator 630.

In exemplary embodiments, the control unit 640 is configured and operative for controlling the signal generator 630 to generate the sequence of stimulating signals in a form of a plurality of electrical pulses. In exemplary embodiments, each of the electrical pulses has a pulse current in a range of between about 10 milliamperes and about 50 milliamperes, and a pulse duration in a range of between about 0.01 millisecond and about 5 millisecond. In exemplary embodiments, the pulse current is in a range of between about 15 milliamperes and about 25 milliamperes, for example, a pulse current of about 20 milliamperes. In exemplary embodiments, the pulse duration is in a range of between about 0.1 millisecond and about 2 millisecond, or optionally between about 0.5 millisecond and about 1 millisecond, or optionally between about 0.8 millisecond and about 1 millisecond. Each of the electrical pulses may have a pulse frequency in a range of between about 25 Hz and about 150 Hz, including, for example, a range of between about 50 Hz and about 70 Hz. In exemplary embodiments, the pulse frequency is about 60 Hz. In exemplary embodiments, each of the electrical pulses may be separated from an adjacent one of the electrical pulses by a time span of at least about 0.5 second. The plurality of electrical pulses may be produced as part of a plurality of electrical pulse trains, whereby each of the electrical pulse trains may include a number of the electrical pulses, and whereby each of the electrical pulse trains has a train pulse duration in a range of between about 0.5 second and about 5 seconds, for example, a train pulse duration of about 1.5 seconds. Optionally, each of the electrical pulse trains is separated from an adjacent one of the electrical pulse trains by a separation time span having a range of between about 0.5 minute and about 60 minutes, including, for example, a separation time span of about 1 minute, or about 2 minutes, or about 5 minutes, or about 10 minutes.

In exemplary embodiments, any of the preceding illustratively described exemplary embodiments of the exemplary implant 600 is suitable for use in generating a distally traveling synthetic esophageal motion within a subject's esophagus, for example, by including any such exemplary embodiment of the implant 600 in any of the hereinabove illustratively described exemplary embodiments of the system for generating a distally traveling synthetic esophageal motion within a subject's esophagus, such as exemplary systems 10 (FIG. 1A), 30 (FIG. 1C), 60 (FIGS. 3A-3D, and 4A-4D), 100 (FIGS. 5A-5D), and 500 (FIG. 8).

In exemplary embodiments, any of the hereinabove illustratively described exemplary embodiments of the system, such as of exemplary systems 10 (FIG. 1A), 30 (FIG. 1C), 60 (FIGS. 3A-3D, and 4A-4D), 100 (FIGS. 5A-5D), and 500 (FIG. 8), and components thereof, may be configured and operative for generating the distally traveling synthetic esophageal motion within the subject's esophagus, wherein the esophagus exhibits different physiological conditions or/and characteristics, for example, wherein the esophagus exhibits characteristics of suspended esophageal peristaltic motility.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference constitutes prior art. To the extent that section headings are used, they should not be construed as necessarily limiting.

What is claimed is:

1. A system for generating a distally traveling synthetic esophageal motion within a subject's esophagus, the system comprising:
    an elongated member sized and configured for nasal or oral placement into the esophagus;
    a series of stimulators mounted or mountable on said elongated member and distributed along a length of said elongated member, said series of stimulators is configured for stimulating a series of portions of the esophagus along an esophageal length spanning between the esophagus LES and UES, and includes at least two longitudinally spaced electrodes, chargeable to opposite polarities and configured for stimulating a portion of the esophagus located therebetween; and a signal generator configured for generating and sending a sequence of stimulating signals to said series of stimulators, so as to evoke a plurality of local independently formed esophageal contractions in a form of a distally traveling synthetic esophageal motion along said esophageal length.

2. The system of claim 1, wherein said signal generator is configured for developing local esophageal pressures of at least 40 mmHg for each of said local independently formed esophageal contractions.

3. The system of claim 1, wherein said elongated member is a medical intubation device.

4. The system of claim 3, wherein said medical intubation device is a gastric feeding tube.

5. The system of claim 1, wherein said series of stimulators is fixed to said elongated member.

6. The system of claim 1, wherein said elongated member includes at least one sensor mounted or mountable on said elongated member.

7. The system of claim 6, wherein at least one said sensor is mounted on said elongated member distally to a distal-most stimulator.

8. The system of claim 6, wherein said at least one sensor comprises at least one of: a pH sensor, a pressure sensor, a manometer, an impedance sensor, a motion sensor, a capacitance sensor, and a mechanical sensor.

9. The system of claim 1, wherein said sequence of stimulating signals includes at least one electrical pulse or electrical pulse train having a magnitude higher than a stimulating threshold in a range of between about 5V and about 20V.

10. The system of claim 1, wherein said signal generator is operatively connected to a control unit.

11. The system of claim 10, wherein said control unit is configured and operative for controlling said signal generator to produce said sequence of stimulating signals being staggered in time such that distally-located stimulators receive stimulating signals after more proximally-located stimulators.

12. The system of claim 10, wherein said control unit is configured and operative for controlling said signal generator to selectively transition said series of stimulators among three states of electrical connectivity.

13. The system of claim 12, wherein said three states correspond to: (i) said series of stimulators connected to said signal generator, (ii) said series of stimulators connected to ground, and (iii) said series of stimulators not connected to said signal generator.

14. The system of claim 1, wherein said plurality of local independently formed esophageal contractions is in a form of a wave of distally progressing contractions within the esophagus.

15. The system of claim 14, wherein said wave of distally progressing contractions includes a second wave starting only after a first wave is finished, without overlapping of said second and first waves.

16. The system of claim 14, wherein said wave of distally progressing contractions includes a second wave beginning before a first wave completes travelling from upper portion of the esophagus.

17. The system of claim 10, wherein said control unit is configured and operative for controlling said signal generator to generate said sequence of stimulating signals in a form of a plurality of electrical pulses, each of said electrical pulses has a pulse current in a range of between about 10 milliamperes and about 50 milliamperes, and a pulse duration in a range of between about 0.01 millisecond and about 5 millisecond.

18. The system of claim 17, wherein each of said electrical pulses has a pulse frequency in a range of between about 25 Hz and about 150 Hz.

19. The system of claim 17, wherein each of said electrical pulses is separated from an adjacent one of said electrical pulses by a time span of at least about 0.5 second.

20. The system of claim 17, wherein said plurality of electrical pulses is produced as part of a plurality of electrical pulse trains, whereby each of said electrical pulse trains comprises a number of said electrical pulses, and whereby each of said electrical pulse trains has a train pulse duration in a range of between about 0.5 second and about 5 seconds.

21. The system of claim 20, wherein each of said electrical pulse trains is separated from an adjacent one of said electrical pulse trains by a separation time span having a range of between about 0.5 minute and about 60 minutes.

22. The system of claim 1, wherein said series of stimulators includes an even number of bipolar electrode pairs in a range of between four bipolar electrode pairs and twenty bipolar electrode pairs.

23. The system of claim 22, wherein said bipolar electrodes pairs are distributable such that a proximal-most electrode pair is locatable proximally to said UES.

24. The system of claim 22, wherein said bipolar electrodes pairs are distributable such that a distal-most electrode pair is locatable distally to said LES.

25. The system of claim 1, configured for generating the distally traveling synthetic esophageal motion wherein the esophagus exhibits characteristics of suspended esophageal peristaltic motility.

26. The system of claim 1, wherein said plurality of local independently formed esophageal contractions has a pattern that simulates a pattern of naturally occurring peristalsis.

27. The system of claim 1, comprising a plurality of longitudinally spaced electrode pairs, wherein each one of said electrode pairs includes two of said longitudinally spaced and oppositely charged electrodes and is configured for stimulating a portion of the esophagus located between said two electrodes.

* * * * *